United States Patent
Zhang et al.

(10) Patent No.: US 10,428,114 B2
(45) Date of Patent: Oct. 1, 2019

(54) TYPE POLYPEPTIDE TARGETING TUMOURS

(71) Applicants: SICHUAN UNIVERSITY, Chengdu, Sichuan (CN); YAOPHARMA CO., LTD., Chongqing (CN)

(72) Inventors: Zhirong Zhang, Sichuan (CN); Tao Gong, Sichuan (CN); Yan Zhang, Chongqing (CN); Xu Song, Sichuan (CN); Tijia Chen, Sichuan (CN); Yao Fu, Sichuan (CN); Xun Sun, Sichuan (CN); Xiaoqing Bai, Chongqing (CN); Bei Zhang, Chongqing (CN)

(73) Assignees: SICHUAN UNIVERSITY, Chengdu, Sichuan (CN); YAOPHARMA CO., LTD., Chongqing (CN)

( * ) Notice: Subject to any disclaimer, the term of this patent is extended or adjusted under 35 U.S.C. 154(b) by 0 days.

(21) Appl. No.: 15/767,146

(22) PCT Filed: Sep. 30, 2016

(86) PCT No.: PCT/CN2016/100989
§ 371 (c)(1),
(2) Date: Apr. 10, 2018

(87) PCT Pub. No.: WO2017/059786
PCT Pub. Date: Apr. 13, 2017

(65) Prior Publication Data
US 2018/0298059 A1 Oct. 18, 2018

(30) Foreign Application Priority Data
Oct. 10, 2015 (CN) .......................... 2015 1 0650649

(51) Int. Cl.
| | | |
|---|---|---|
| C07K 7/50 | (2006.01) | |
| A61K 47/42 | (2017.01) | |
| A61K 47/64 | (2017.01) | |
| A61K 38/12 | (2006.01) | |
| A61K 35/00 | (2006.01) | |
| A61P 35/00 | (2006.01) | |

(52) U.S. Cl.
CPC ................ C07K 7/50 (2013.01); A61K 38/12 (2013.01); A61K 47/42 (2013.01); A61K 47/64 (2017.08); A61P 35/00 (2018.01)

(58) Field of Classification Search
None
See application file for complete search history.

(56) References Cited

FOREIGN PATENT DOCUMENTS

| CN | 101879313 | * | 5/2009 | ............ A61K 47/48 |
|---|---|---|---|---|
| CN | 10313087 A | | 6/2013 | |
| CN | 105294831 A | | 2/2016 | |

OTHER PUBLICATIONS

Hong et al. CN101879313 English abstract. 4 pages. (Year: 2009).*
International Search Report for PCT/CN2016/100989, dated Dec. 27, 2016, ISA/CN.
Song, Xu et al., "Development of a Multi-Target Peptide for Potentiating Chemotherapy by Modulating Tumor Microenvironment", Biomaterials, No. 108, Sep. 4, 2016 (Sep. 4, 2016), ISSN: 0142-9612, see the whole document.
Liu, Ze et al., "Legumain Protease-Activated TAT-Liposome Cargo for Targeting Tumours and their Microenvironment", Nature Communications, Jun. 27, 2014 (Jun. 27, 2014), ISSN: 2041-1723, see abstract.
Zhao, Bo et al., "Cellular Toxicity and Anti-Tumor Efficacy of iRGD Modified Doxorubixin Loaded Sterically Stabilized Liposomes", Acta Pharmaceutica Sinica, vol. 48, No. 3, Mar. 31, 2013 (Mar. 31, 2013), ISSN: 0513-4870, see p. 418, left column, paragraph 2 and p. 422, left column, paragraph 2.
Li, Bin et al., "Advances in Research of Tumor-Targeting Peptide Drugs Based on Antibodies and Ligands", Chinese Medicinal Biotechnology, vol. 9, No. 4, Aug. 31, 2014 (Aug. 31, 2014), ISSN: 1673-713X, see the whole document.
An, Lianxiao et al., Advances in Research of RGD Peptide as Drug Targeting Ligand, Chinese Journal of Biochemical Pharmaceutics, vol. 31, No. 1, Jan. 31, 2010 (Jan. 31, 2010), ISSN: 1005-1678, see the whole document.
Douglas Hanahan et al.,"Hallmarks of cancer: the next generation", Cell 2011, 144, Mar. 4, 2011(Mar. 4, 2011), 647-674.
Kazuki N. Sugahara et al. "Coadministration of a Tumor-Penetrating Peptide Enhances the Efficacy of Cancer Drugs". Science, May 21, 2010(May 21, 2010); 328(5981):1031-5.
Gavin P. Dunn et al. "Cancer immunoediting: from immunosurveillance to tumour escape", Nature immunology, Nov. 2002, 3(11):991-8.
Debbie Liao et al. "Synthetic enzyme inhibitor: a novel targeting ligand for nanotherapeutic drug delivery inhibiting tumor growth without systemic toxicity". Nanomedicine. 7 (2011), 665-673 (2011).
Chen Tijia et al:"nRGD modified lycobetaine and octreotide combination delivery system to overcome multiple barriers and enhance anti-glioma efficacy",Colloids and Surfaces. B, Biointerfaces, Elsevier, Amsterdam, NL, vol. 156, May 15, 2017,pp. 330-339.
European Search Report dated May 2, 2019.
Ralph A. Reisfeld, "The tumour microenvironment: a target for combination therapy of breast cancer". Crit. Rev. Oncog. 18, 115-133 (2013).

(Continued)

*Primary Examiner* — Marcela M Cordero Garcia

(74) *Attorney, Agent, or Firm* — Yue (Robert) Xu; Apex Attorneys at Law, LLP

(57) ABSTRACT

Provided is a nRGD polypeptide formed by connecting alanine-alanine-asparagine (AAN) and a polypeptide containing arginine-glycine-aspartic acid (RGD), wherein the nRGD polypeptide can target tumor vessels, tumor cells and tumor-associated macrophages, and mediate the targeted delivery of tumors.

10 Claims, 23 Drawing Sheets

Specification includes a Sequence Listing.

(56) References Cited

OTHER PUBLICATIONS

Yingying Lin et al. "Selective ablation of tumor-associated macrophages suppresses metastasis and angiogenesis". Cancer Sci. 104, Sep. 2013, 1217-1225.

Setg B. Coffelt et al. "Tumor-associated macrophages: Effectors of angiogenesis and tumor progression". Biochimica et Biophysica Acta. 1796 (2009) 11-18.

* cited by examiner

TYPE POLYPEPTIDE TARGETING TUMOURS

CROSS REFERENCE TO RELATED APPLICATIONS

This application is the national phase of International Application No. PCT/CN2016/100989, titled "A NEW TYPE POLYPEPTIDE TARGETING TUMOURS", which claims the priority of Chinese Patent Application No. 201510650649.2, filed on Oct. 10, 2015 with the State Intellectual Property Office of People's Republic of China, and titled with "A NEW TYPE POLYPEPTIDE TARGETING TUMOURS", and the disclosures of which are hereby incorporated by reference.

FIELD

The present invention belongs to the field of medicine, relating to a novel tumor-targeting polypeptide, specifically to a tandem polypeptide nRGD formed by connecting alanine-alanine-asparagine (AAN)-containing sequence to a arginine-glycine-aspartic acid (RGD)-containing peptide, which not only targets tumour cells and vessels, but also targets tumour-associated macrophages, therefore regulating tumour microenvironment and enhancing anti-tumour effect.

BACKGROUND

The tumour site has a special microenvironment that provides the necessary conditions for the development and metastasis of the tumour, for example, maintaining growth-promoting signals, maintaining neovascularization, counteracting apoptosis and growth-inhibitory signals, tumour cell metastasis and infinite proliferation, genome instability and mutagenesis, energy metabolism reintegration, inflammation which promotes tumour growth, and escaping the identification and killing from immune system. (Hanahan D, Weinberg R A. Hallmarks of cancer: the next generation. Cell 2011, 144, 647-674.)

With the rapid development of biomedical technology, tumor-targeting therapy has become the main development direction of current cancer treatment. The development of drug delivery vector technology offers the possibility of specific, targeted delivery of anti-tumour drugs. The use of specific tumour-targeting ligands to modify anti-tumour drugs or drug delivery vectors can effectively increase the distribution and accumulation of drugs or drug delivery vectors in tumour sites and reduce the distribution of drugs in non-target organs and tissues, thereby achieving enhanced antitumour efficacy and reduced side effects.

Integrin is a type of cell adhesion receptor that exists on the cell membrane. It is a tumour-penetrating peptide, and its main function is to mediate the adhesion among cells, and between cells and extracellular matrix. Integrins form heterodimers by the non-covalent bonding of the $\alpha$ and $\beta$ subunits. In vertebrate bodies, 18 $\alpha$ subunits and 8 $\beta$ subunits form 24 different heterodimers. Among them, $\alpha v \beta 3$ integrins are highly expressed on the surface of many tumour cells, such as ovarian cancer, melanoma, breast cancer, glioma and tumour-associated vascular endothelial cells, and are closely related to tumour neovascularization and metastasis.

Studies have confirmed that tripeptide sequence containing arginine-glycine-aspartic acid (RGD) can specifically recognize and bind integrins. At present, the commonly used tumour-penetrating peptide iRGD has the characteristics of simultaneously targeting tumour blood vessels and tumour cells, through tightly binding with the highly expressed integrin receptor proteins $\alpha v \beta 3$ and $\alpha v \beta 5$ on the membrane of tumour neovascular endothelial cells to achieve tumour targeting of anticancer drugs. (Sugahara K N, Teesalu T, Karmali P P, Kotamraju V R, Agemy L, Greenwald D R, Ruoslahti E. Coadministration of a tumour-penetrating peptide enhances the efficacy of cancer drugs. Science 2010 May 21; 328(5981):1031-5.)

The prior art discloses that tumour cells interact with organisms during the development of malignant tumours. Tumour cells use their own high mutability, on the one hand, to down-regulate the expression of immunorecognition and attack related proteins to achieve immune escape; on the other hand, to express abnormal or over-express immunosuppressive related proteins, thereby directly inhibiting tumour immune responses, or inducing the differentiation and infiltration of immunosuppressive cells. In this process, tumour cells not only overcome the recognition and killing by the immune system, but also establish a tumour immune microenvironment that can provide sufficient nutrition for its rapid growth. (Dunn G P, Bruce A T, Ikeda H, Old L J, Schreiber R D. Cancer immunoediting: from immunosurveillance to tumour escape. Nat Immunol. 2002 November; 3(11):991-8.)

It can be seen that although RGD peptides target tumour blood vessels and tumour cells, thereby enhancing the antitumour efficacy. Biological treatment of tumours is also an nonnegligible aspect. Tumour cells establish their own immune barriers, so that the body cannot recognize or kill the tumour cells. As long as there are residual tumour cells, the tumour may recur. Moreover, the ideal therapeutic effect cannot be achieved merely through a single cancer therapy.

In order to solve at least one of the aforementioned problems, the present invention provides a more effective novel tumour-targeting polypeptide.

SUMMARY

One of the objects of the present invention is to provide a novel multifunctional polypeptide for tumour targeting. The polypeptide is formed by linking an alanine-alanine-asparagine (AAN)-containing sequence to an RGD-containing peptide, preferably through a covalent bond, to obtain a tandem polypeptide nRGD which targets tumour cells, tumour vessels and tumour-associated macrophages, thereby regulating tumour microenvironment and enhancing antitumour effect.

In the study, the inventors connected iRGD peptides that possesses highly prominent effect on tumour and tumour vessel targeting with AAN that targets tumour-associated macrophages to obtain nRGD through covalent bond, and then used doxorubicin (Dox) as a model drug to prepare a drug-containing liposome.

Surprisingly, the study found that compared with the drug-containing liposomes prepared from iRGD and doxorubicin (Dox), the drug-containing liposomes prepared from nRGD polypeptide and doxorubicin (Dox) achieved unexpected antitumour effects. The inventors have administered the nRGD polypeptide in combination with Dox or Dox liposomes and have also observed significant antitumour effects.

One of the objects of the present invention is to provide a novel tumour-targeting polypeptide (nRGD) which can be directly used in combination with a drug or a carrier.

One of the objects of the present invention is to provide a novel tumour-targeting polypeptide (nRGD) which can be used to modify an anti-tumour drug to obtain a prodrug of the anti-tumour drug and modify a drug delivery carrier.

One of the objects of the present invention is to provide a novel tumour-targeting polypeptide which targets tumour-associated macrophages through an alanine-alanine-asparagine (AAN) peptide.

One of the objects of the present invention is to provide a novel tumour-targeting polypeptide which targets tumour blood vessels and tumour cells through a RGD polypeptide.

One of the objects of the present invention is to provide a novel tumour-targeting polypeptide, wherein the AAN-containing sequence is preferably covalently linked to the RGD-containing peptide; or preferably by peptide bond or amino acid peptide chain; or AAN-containing sequence is linked to the RGD-containing peptide by —$CH_2NH$—, —$CH_2S$—, —$CH_2$—$CH_2$—, —CH=CH—, —$COCH_2$— and —$CH(OH)CH_2$—. It should be understood that the AAN- and RGD-containing peptides may be linked by amino acid analogs or peptide analogs, and more than one atom may be located between the bonding atoms, such as by gamma-aminobutyric acid linkage.

The "novel multifunctional polypeptide" described in the present invention has the same meaning as "novel polypeptide", "multifunctional polypeptide", "nRGD", "nRGD polypeptide" and "polypeptide nRGD".

The "RGD-containing peptide" described in the present invention has the same meaning as the "peptide containing RGD", "RGD-containing peptide chain" and "peptide chain-containing RGD".

The AAN described in the present invention is a substrate of an legumain. The target of the AAN of the present invention is legumain. Legumain is widely present in tumour cells and in the tumour microenvironment, which is activated in acidic (pH=4.0 to 6.5) environment and inactivated in neutral environment.

Studies found that legumain colocalizes with most integrin receptors such as αvβ3 to form complexes, which are highly expressed on both tumour cells and tumour neovascular endothelial cells. Various types of tumours, such as breast cancer, colon cancer, lung cancer and liver cancer, overexpress legumain.

Further studies found that tripeptide substrates containing alanine-alanine-asparagine (AAN) sequence can be specifically recognized and digested by legumain.

More importantly, the target of AAN of the present invention is legumain. In the tumour environment, the expression site of legumain can be transferred from the cytoplasm to the cell surface. (Liao, D. et al. Synthetic enzyme inhibitor: a novel targeting ligand for nanotherapeutic drug delivery inhibiting tumour growth without systemic toxicity. Nanomedicine. 7, 665-673 (2011).) Legumain is not only highly expressed in tumour cells but also in tumour-associated macrophages which are associated with the tumour microenvironment. (Reisfeld, R. A. The tumour microenvironment: a target for combination therapy of breast cancer. Crit. Rev. Oncog. 18, 115-133 (2013). Lin, Y. et al. Selective ablation of tumour-associated macrophages suppresses metastasis and angiogenesis. Cancer Sci. 104, 1217-1225 (2013).)

Patent Application No. CN201310048238 states that the AAN tripeptide modified doxorubicin prodrug has the same anti-tumour efficacy as the original drug. The literature also shows that the direct modification of liposomes by AAN does not improve the antitumour efficacy of the drug (Ze Liu, Min Xiong, Junbo Gong, Yan Zhang, Nan Bai, Yunping Luo, Luyuan Li, Yuquan Wei, Yanhua Liu, Xiaoyue Tan & Rong Xiang. Legumain protease-activated TAT-liposome cargo for targeting tumours and their microenvironment. Nat Commun. 2014; 5 4280.). Thus, as a target, only AAN tripeptide cannot successfully improve the antitumour effects of the anticancer drugs or carriers.

The novel polypeptide of the present invention can also target tumour-associated macrophages (TAMs). TAMs are important inflammatory cells that exist in the blood vessels around tumour sites and in the necrotic areas without tumour blood vessels. TAMs are key components of tumour sites, which secrete a large number of tumour growth promoting factors. It has also been found in mouse models that TAMs regulate angiogenesis, lymphangiogenesis, immunosuppression and tumour metastasis. (Seth B. Coffelt, Russell Hughes, Claire E. Lewis. Tumour-associated macrophages: Effectors of angiogenesis and tumour progression. Biochimica et Biophysica Acta. 1796 (2009) 11-18) Along with other cells such as bone marrow-related cells associated with tumour sites, TAMs have become a very attractive target for novel cancer biotherapies.

At present, there are three main aspects of the therapies through TAMs: inhibiting the accumulation of monocytes at tumour sites, eliminating the macrophages at tumour sites, and neutralizing the key cytokines secreted by TAMs. These are all single ways of treating tumours with TAMs. (Seth B. Coffelt, Russell Hughes, Claire E. Lewis. Tumour-associated macrophages: Effectors of angiogenesis and tumour progression. Biochimica et Biophysica Acta 1796 (2009) 11-18)

The novel polypeptide of the present invention not only targets tumour blood vessels and cells to kill tumour blood vessels and cells, but also targets tumour-associated macrophages, thereby significantly enhancing the therapeutic effect by changing the tumour microenvironment.

The novel multifunctional polypeptide of the present invention can not only be combined with other therapeutic methods for anti-tumour, but also can be used alone as an anti-tumour biological treatment method.

In addition to peptide chains, AAN-containing sequences and RGD-containing peptides are also linked by molecules similar to, but not the natural peptide chain. Linkage of amino acids or amino acid analogues includes but is not limited to —$CH_2NH$—, —$CH_2S$—, —$CH_2$—$CH_2$—, —CH=CH—, —$COCH_2$— and —$CH(OH)CH_2$—. The tumour targeting and tumour vasculature targeting functions of RGD would not be affected, whether or not AAN breaks from the RGD peptide chain.

One of the objects of the present invention is to provide a pharmaceutical composition, wherein the polypeptide nRGD is mixed with an active pharmaceutical active ingredient, or with a drug carrier.

One of the objects of the present invention is to provide a pharmaceutical composition, wherein the polypeptide nRGD is either covalently linked to or non-covalently associated with the active pharmaceutical ingredient, or the polypeptide nRGD is either covalently linked to or non-covalently associated with the drug delivery carrier.

The function mode of nRGD polypeptide in the present invention includes: mixing with the composition without covalent link or through non-covalent association; connecting to the composition through covalent link or non-covalent association; administrating the novel polypeptide before or after the administration of the composition; linking the composition; one manner of the above or a mixture thereof.

As one of the specific embodiments of the present invention, the nRGD polypeptide of the present invention can be used in combination with one or more auxiliary molecules.

Preferably, the combination is association; at least one of the auxiliary molecules does not overlap with the nRGD polypeptide; at least one of the auxiliary molecules overlaps with the nRGD polypeptide.

Preferably, the auxiliary molecule includes separate homing molecule, targeting molecule, affinity ligand, cell penetrating peptide, in vivo escape molecule, subcellular targeting molecule, nuclear targeting molecule, or a conjugate and mixture thereof.

Herein, "homing molecule" means that it preferentially homes to tumours or other specific tissues in the body in preference to normal tissues; "conjugate" refers to a substance formed by chemical bonds between molecules.

Drugs suitable for use in the present invention include, but are not limited to the drugs having a therapeutic effect on tumours: therapeutic proteins, therapeutic compounds, therapeutic compositions, cancer chemotherapeutics, toxins, cytotoxic agents, anti-inflammatory agents, growth factors, cytokines, chemokines, compounds modulating one or more signaling pathways, antibodies, nucleic acids, nucleic acid analogues, cells, viruses, bacteriophages, virus particles, bacteriophage particles, virus capsids, phage capsids, virus-like particles, liposomes, microspheres, nanoparticles, micelles, emulsions, microemulsions, dendrimers, microparticles, chemotherapeutic agents and anti-angiogenic agents, or a conjugate and mixture thereof.

Tumours suitable for the present invention include but are not limited to benign or malignant tumours, including benign or malignant tumors of epithelial tissue; benign or malignant tumors of mesenchymal tissue; benign or malignant tumors of lymphoid and hematopoietic tissue; benign or malignant tumors of nervous tissue; gonad or embryo-related benign or malignant tumors; and other tumours, including pigmented nevus, hydatidiform mole, melanoma, chorionic epithelioma, seminoma, dysgerminoma and embryonal carcinoma.

In a specific embodiment, the RGD peptide chain contained in the nRGD peptide of the present invention includes but is not limited to: RGD peptide, cyclic c(RGDfK) (SEQ ID NO: 1), iRGD (SEQ ID NO: 2), or a derivative thereof, preferably iRGD.

The peptide nRGD of the present invention can be covalently linked to an active pharmaceutical ingredient or a drug delivery carrier via cysteine residue

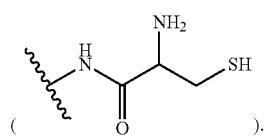 [SMILES: *NC(=O)C(N)CS]

Preferred peptide nRGD has the structure shown in Formula 1:

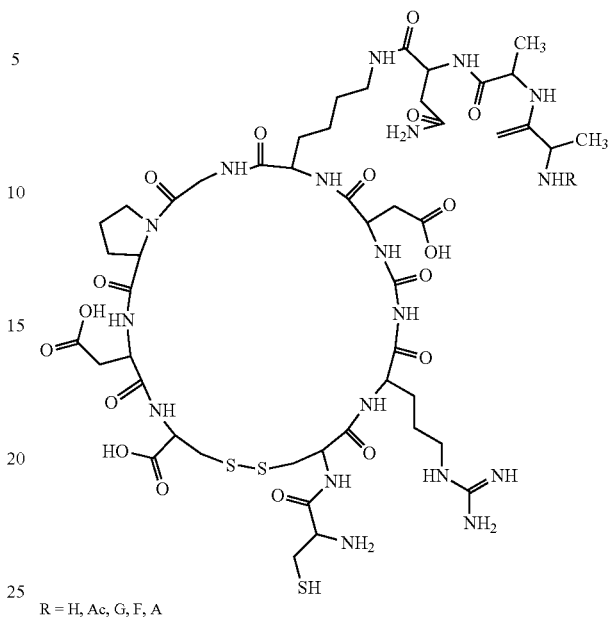

Formula 1

R = H, Ac, G, F, A

The peptide nRGD of the present invention may not contain the above-mentioned cysteine residue when it is non-covalently associated with or used in combination with an active pharmaceutical ingredient or a drug delivery carrier.

As one of the preferred embodiments, the AAN in the novel targeting polypeptide includes its derivatives, such as polypeptide substrate R-AAN sequence which is susceptible to legumain, wherein the R group is a hydrogen atom (H), acetyl (Ac), alanine (A), phenylalanine (F), glycine (G) or a conjugate thereof. In the R-AAN-sequence, R is preferably H, and the sequence of nRGD is CCRGDK(NAA)GPDC (SEQ ID NO: 3), wherein the second cysteine and the tenth cysteine are linked into a ring; alternatively, R is preferably H, and the sequence of nRGD is CRGDK (NAA) GPDC (SEQ ID NO: 4), wherein the two cysteines are linked into a ring.

As one of the preferred embodiments, the drug used is preferably a chemotherapeutic drug, wherein the chemotherapeutic drug is preferably doxorubicin (Dox).

As one of the preferred embodiments, the pharmaceutical dosage form used in the present invention is preferably a PEGylated liposome.

As one of the preferred embodiments, the combinatory use of polypeptide nRGD and an active pharmaceutical ingredient or a drug delivery carrier in the present invention is by means of covalent link and direct mixing.

As one of the preferred embodiments, the tumour model for which the polypeptide nRGD and an active pharmaceutical ingredient or a drug delivery carrier are used in the present invention is xenograft breast tumor model.

One of the objects of the present invention is to provide the use of the polypeptide nRGD or a pharmaceutical composition thereof in the preparation of an anti-tumour drug.

One of the objects of the present invention is to provide the use of the polypeptide nRGD or a pharmaceutical composition thereof in the preparation of a pharmaceutically acceptable pharmaceutical preparation.

The addition of the multifunctional polypeptide of the present invention significantly increases the anti-tumour effect of the doxorubicin original drug and the doxorubicin liposome. Moreover, the anti-tumour effect of nRGD and iRGD also increases significantly. Also, the addition of multifunctional peptides also significantly increases the survival of mice. It was found that most of the mice in the nRGD group have a survival period of 90 days, and some of the tumours in the mice have even disappeared. This result is surprising, and such significant effect has not been reported in previous anticancer drug treatments. Although by a simple mixture, the survival time of some mice in the PEGylated liposome group and nRGD mixed drug group was also extended to 90 days, while the mice in the iRGD group only survived for 2 months. The addition of multifunctional peptide significantly reduces drug toxicity due to the increased targeting.

In the present invention, through creative research, an alanine-alanine-asparagine (AAN)-containing sequence is covalently linked to an RGD-containing peptide to obtain a tandem polypeptide (nRGD) which targets the tumour cells, tumour vessels and tumour-associated macrophages to regulate tumour microenvironment and enhance anti-tumour effect. Using doxorubicin and liposome, lycobetaine and nanostructured lipid carrier, paclitaxel and albumin nanoparticle, and docetaxel and polymer micelle as model drugs, through mixing or covalently linking, the polypeptide of the present invention has achieved a significant anti-tumour effect in the treatment of mouse xenograft breast tumor.

Thus, the polypeptide of the present invention significantly increases the effect of anti-tumour components while also alters the single treatment manner of anti-tumour components, showing a good application prospect.

The advantages of the present invention are as follows:

(1) The multifunctional polypeptide nRGD of the present invention significantly improves the effect of anti-tumour components.

(2) The multifunctional polypeptide nRGD of the present invention can improve the effect of anti-tumour components by targeting tumour-associated macrophages, regulating the tumour microenvironment, and producing biotherapeutic effects.

(3) The multifunctional polypeptide nRGD of the present invention changes the single treatment manner of anti-tumour components.

(4) The multifunctional polypeptide of the present invention reduces the toxicity of the anti-tumour component while increasing the targeting ability.

(5) The multifunctional polypeptide of the present invention is easy to use and expected to be a key component in the development of anti-tumour drugs in the future.

BRIEF DESCRIPTION OF DRAWINGS

As follows, embodiments of the present invention will be described in detail with reference to the accompanying drawings.

FIG. 1-1 shows a schematic diagram of doxorubicin liposome; FIG. 1-2 is an image of doxorubicin liposome under electron micrograph.

FIG. 2-1 to FIG. 2-6 show in 4T1 tumour model, nRGD group significantly improves the efficacy of doxorubicin. FIG. 2-1 shows the growth curve of tumour; FIG. 2-2 shows the image of tumour; FIG. 2-3 shows the weight of tumour; FIG. 2-4 shows the inhibition rate; FIG. 2-5 shows the changes of body weight; FIG. 2-6 shows the growth curve. *P<0.05, ***P<0.01.

FIG. 3-1 to FIG. 3-4 show the tumour evaluation by HE staining, immunohistochemical staining of Ki-67 and HER2. FIG. 3-1 shows HE staining, the yellow arrow indicates the area where tumour growth is active; FIG. 3-2 shows Ki-67 immunohistochemical staining; FIG. 3-3 shows HER2 immunohistochemical staining; FIG. 3-4 shows the signal density measurements of Ki-67 and HER2.

FIG. 4-1 to FIG. 4-5 show that the nRGD group can identify tumour vessels, increase tumour penetration, target and kill tumour-associated macrophages. FIG. 4-1, FIG. 4-2 and FIG. 4-3 show that nRGD-Lipo-Dox targets CoCl2-treated 4T1 and M2 type macrophages. *P<0.05, ***P<0.01. FIG. 4-4 are tumour sections showing that the nRGD group increases the accumulation of tumour sites and normalize tumour-associated blood vessels. Scale bar, 200 μm. Green, Dox; red, CD34. FIG. 4-5 are tumour sections showing that the nRGD group reduces the TAMs infiltrating tumour sites. Scale bar, 200 μm. Red, CD206; blue, DAPI-stained nucleus.

FIG. 5-1 to FIG. 5-6 show the level of cytokines at the tumour site after treatment. FIG. 5-1 shows the ELISA assay for TGF-β1. *P<0.05, ***P<0.01. FIG. 5-2 shows TGF-β1; FIG. 5-3 shows CCl2; FIG. 5-4 shows IL-10; FIG. 5-5 shows IL-6; FIG. 5-6 shows TNF-α (n=3).

FIG. 6-1 to FIG. 6-6 show that the nRGD group targets TAMs to regulate the tumour microenvironment. FIG. 6-1 shows VEGF immunohistochemical staining (magnification 100×). Inhibition of angiogenesis is assessed by immunofluorescent staining for CD34 (FIG. 6-2) and CD 105 (FIG. 6-3) (red). Changes in the immune microenvironment are evaluated through CD8+ T cells (red) (FIG. 6-4), CD4+ (green)/Foxp3+ (red) regulatory T cells (yellow) (FIG. 6-5) and CD11b+(green)/Gr-1+(red) MDSCs (yellow) (FIG. 6-6. The nuclei were stained blue by DAPI. Scale bar, 200 μm.

FIG. 7-1 to FIG. 7-4 show that the nRGD group has relatively low toxicity. FIG. 7-1 shows sections from different tissues (200× magnification, except for bone 100× magnification); FIG. 7-2 shows splenomegaly in each group; FIG. 7-3 shows serum cytokine IL-6 measurement; FIG. 7-4 shows serum cytokine IL-12 measurement. *P<0.05, ***P<0.01.

FIG. 8-1 to FIG. 8-5 show that in the 4T1 tumour model, the nRGD group significantly increases the efficacy of paclitaxel. Growth curve of tumour (FIG. 8-1), image of tumour (FIG. 8-2), weight of tumour (FIG. 8-3), tumour inhibition rate (FIG. 8-4), weight change (FIG. 8-5). *P<0.05, ***P<0.01.

FIG. 9-1 to FIG. 9-5 show that in the 4T1 tumour model, the nRGD group significantly increases the efficacy of lycobetaine. Growth curve of tumour (FIG. 9-1), image of tumour (FIG. 9-2), weight of tumour (FIG. 9-3), tumour inhibition rate (FIG. 9-4), weight change (FIG. 9-5). *P<0.05, ***P<0.01.

FIG. 10-1 to FIG. 10-5 show that in the 4T1 tumour model, the nRGD group significantly increases the efficacy of docetaxel. Growth curve of tumour (FIG. 10-1), image of tumour (FIG. 10-2), weight of tumour (FIG. 10-3), tumour inhibition rate (FIG. 10-4), weight change (FIG. 10-5). *P<0.05, ***P<0.01.

DETAILED DESCRIPTION

Example 1

Synthesis of Peptide nRGD

The peptide was synthesized by solid-phase synthesis, which has the sequence of CCRGDK(NAA)GPDC (SEQ ID NO:4), in which the second cysteine and the tenth cysteine formed a ring. (Synthesized by GL Biochem. (Shanghai) LTD.) The purity of the obtained peptide nRGD was 85%.

The peptide nRGD may not include the first cysteine of the linking group when it was non-covalently associated or used in combination with an active pharmaceutical ingredient or a drug delivery carrier, and the corresponding sequence was CRGDK(NA)GPDC (SEQ ID NO: 4), wherein the two cysteines were linked into a ring. The purity of the obtained nRGD peptide was 92%.

Example 2

Preparation and Characterization of Doxorubicin Liposomes

Doxorubicin liposomes were prepared by membrane dispersion method and ammonium sulfate gradient method. 56 parts of phospholipids, 34 parts of cholesterol, 8 parts of PEG2000-DSPE (Lipoid, Germany) and 2 parts of Mal-PEG2000-DSPE (Lipoid, Germany) were dissolved in 5 mL of chloroform. For PEGylated liposomes, there was no addition of Mal-PEG2000-DSPE, and the formula was: 56 parts of phospholipids, 34 parts of cholesterol, 10 parts of PEG2000-DSPE. The mixture was rotated and evaporated to remove the organic solvent and then hydrated by adding 123 mM ammonium sulfate solution. The mixture was sonicated by the probe and eluted with G75 and incubated with Dox for 8 hours. After removal of non-encapsulated doxorubicin, unmodified Mal-containing liposomes and PEGylated liposomes (PEG-Lipo-Dox) were obtained. These liposomes were incubated with the corresponding polypeptides (molar ratio of peptide: MAL-PEG2000-DSPE=5:1) for 4 h, and then the unreacted polypeptides were removed by passing through a Sepharose CL-4B column to obtain iRGD liposomes (iRGD-Lipo-Dox) and nRGD liposomes (nRGD-Lipo-Dox). The particle size and potential were measured by a Malvern particle sizer, and the morphology was characterized by transmission electron microscopy. The entrapment rates were determined by ultrafiltration.

Figure 1:
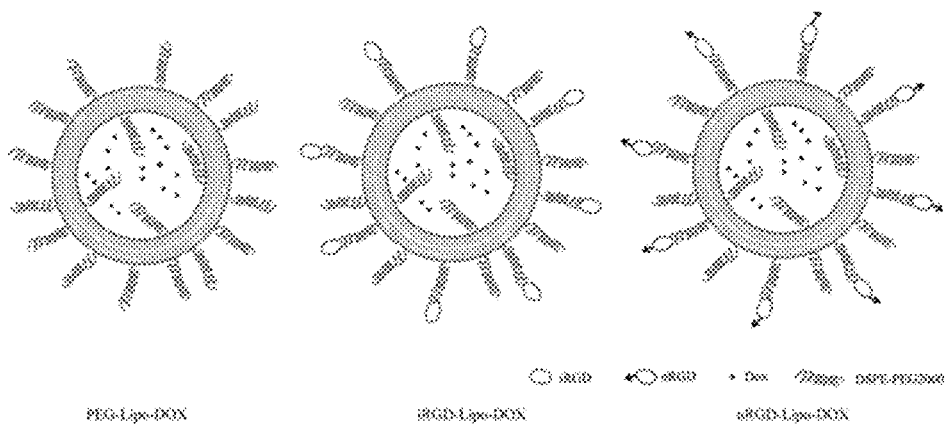
FIG. 1-1 to FIG. 1-2 show the schematic and electron microscopy images of doxorubicin liposome.

The results are shown in Table 1. All liposomes were about 150 nm, negatively charged. The potential of iRGD liposomes (iRGD-Lipo-Dox) and nRGD liposomes (nRGD-Lipo-Dox) was increased compared to PEGylated liposomes (PEG-Lipo-Dox). The entrapment rates of all liposomes were greater than 90%. As shown in FIG. 1, the resulting liposomes were round in shape and uniform in size.

TABLE 1

Properties of liposomes (n = 3)

| | Particle Size (nm) | Multi-scattering Coefficient | Zeta Potential (mv) | Entrapment Rate (%) |
|---|---|---|---|---|
| PEG-Lipo-Dox | 152.4 ± 7.8 | 0.280 ± 0.038 | −22.5 ± 1.2 | 93.1 ± 4.2 |
| iRGD-Lipo-Dox | 166.8 ± 6.9 | 0.234 ± 0.009 | −11.4 ± 0.6 | 96.1 ± 2.5 |
| nRGD-Lipo-Dox | 152.8 ± 8.3 | 0.206 ± 0.009 | −13.6 ± 0.1 | 97.9 ± 1.9 |

Example 3

Evaluation of Pharmacodynamics and Toxicity of Doxorubicin and its Liposomes

Female Balb/c mice were inoculated with $5 \times 10^5$ 4T1 cells and randomly divided into 7 groups: saline group (NS), Dox group, PEG-Lipo-Dox group, iRGD-Lipo-Dox group, nRGD-Lipo-Dox group, Dox and nRGD coadministration group (Dox+nRGD), PEGylated liposome and nRGD coadministration group (PEG-Lipo-Dox+nRGD). The mice were injected with 5 mg/kg Dox equivalents of drugs or various formulations on day 8 and day 12. The single dose of the coadministration group included two shoots; one shoot was an equivalent drug or formulation of 5 mg/kg Dox, while the other shoot was 4.8 mg/kg nRGD. The volume and body weight of the mice were measured every two days. Some mice were sacrificed for mechanism and toxicity study on day 20. The average tumour growth inhibition (TGI) was calculated after tumour weighing: TGI=(1−(mean tumour weight of treatment group/(average tumour weight of control group))×100%. The antitumour effect and mechanism were studied by HE, immunohistochemistry, RT-PCR, immunofluorescence and ELISA. Plasma samples were collected for ELISA detection. Tissue samples were evaluated for toxicity by HE staining. The remaining mice were studied for survival time.

Results:

1. The nRGD group improved anti-tumour effects whether it was directly mixed with Dox and liposomes or modified on the surface of liposome.

Figures 1, 2:
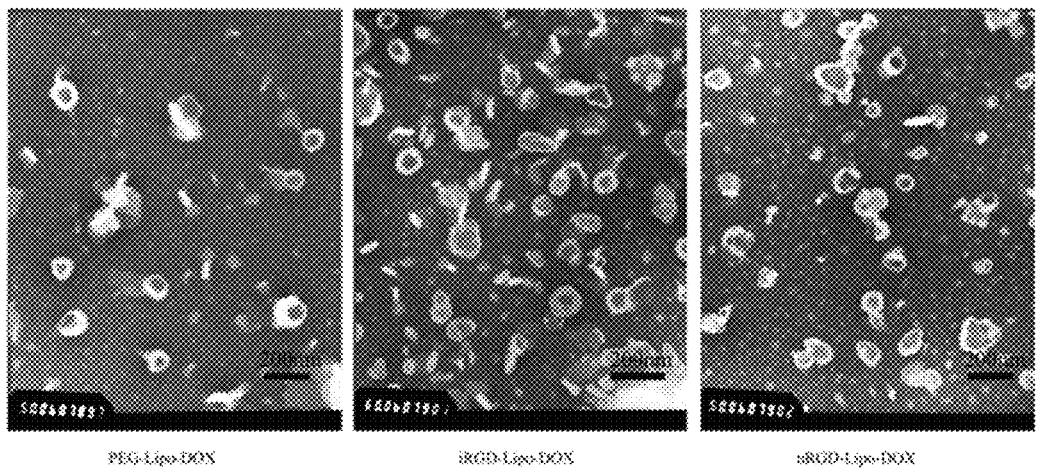

As shown in FIG. 2, 4T1 tumours rapidly increased to 2161.7±422.6 mg in 20 days without treatment, with a volume of 1200 mm³. The tumours size in the treatment groups decreased. Compared with the iRGD-Lipo-Dox group, both PEG-Lipo-Dox+nRGD and nRGD-Lipo-Dox groups exhibited significant anti-tumour effects. The anti-tumour effect of the peptide-added groups was also improved compared with the groups without adding peptide. The tumour growth inhibition rates were also consistent with the tumour growth curves. The tumour weight of nRGD-Lipo-Dox group was 49.8±28.6 mg, and the inhibition rate was as high as 97.7%. The tumour weights of Dox and PEG-Lipo-Dox groups were 1592.0±98.0 mg and 942.0±295.0 mg, and the inhibition rates were only 26.3% and 56.4%, respectively. Tumours in the Dox+nRGD group and the PEG-Lipo-Dox+nRGD group were only 462.0±43.2 mg and 195.0±116.1 mg, and the inhibition rates were 77.5% and 90.1%, respectively. Consistent with the anti-tumour experiments, nRGD group can extend the survival time of tumour mice. For the nRGD-Lipo-Dox group, 44.4% of the mice survived after 90 days and the tumours of the mice were completely cured. The survival time of mice in the nRGD coadministration group was also longer than that of the control group. The iRGD-Lipo-Dox group only survived 65 days. As can be concluded from the above experiments, the anti-tumour effect of the nRGD group is excellent.

Figures 1, 2:
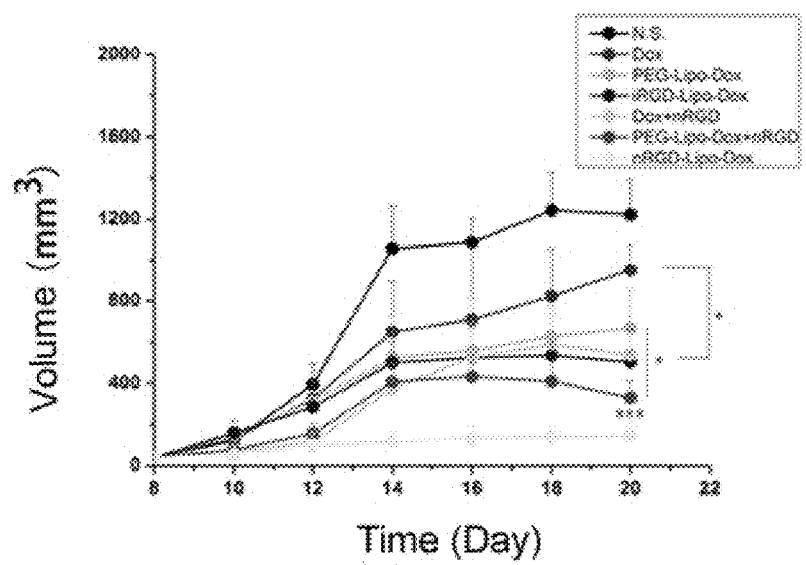
Figure 2:
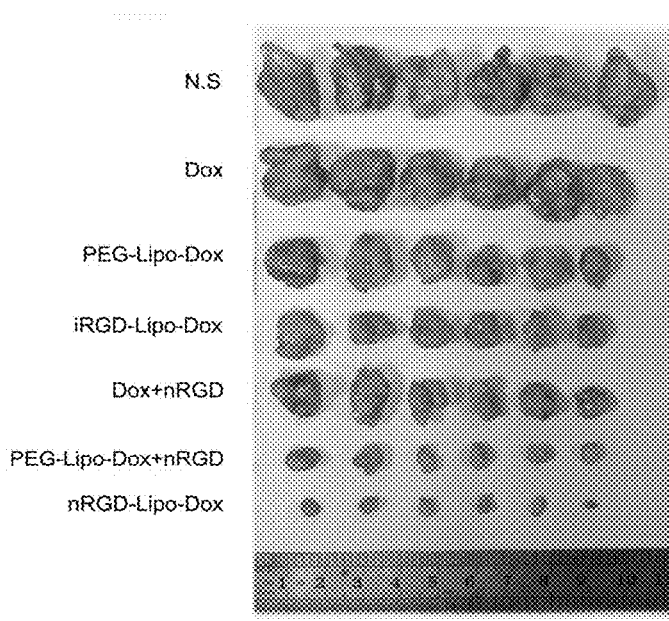
Figures 2, 3:
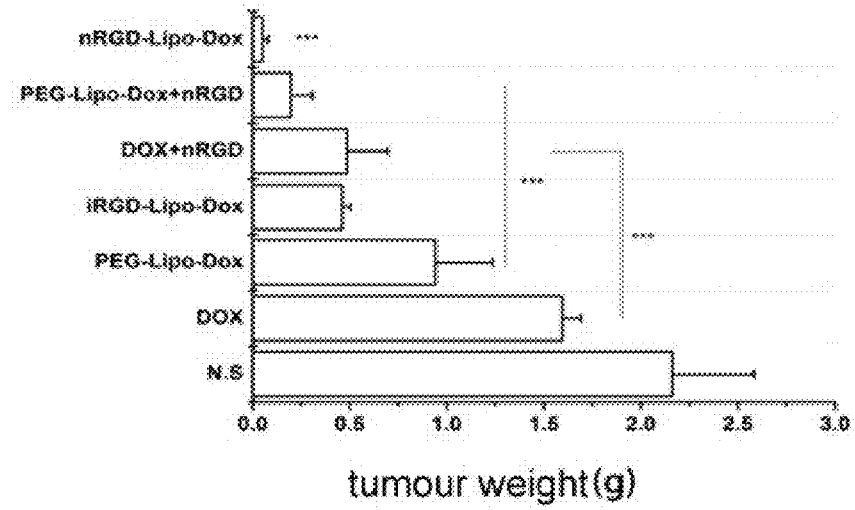

Based on the above results, in order to further confirm the anti-tumour effect of nRGD, the inventors performed HE and immunohistochemical studies on the tumour, as shown in FIG. 3. HE staining showed that the nRGD group significantly inhibited the tumour growth, and basically all the tumours in nRGD-Lipo-Dox group were necrotic. Ki-67 immunohistochemistry is to evalutate of actively reproducing cells and HER2 immunohistochemistry is to assess oncogenic transforming factors and tumour growth. Both methods also confirmed that the nRGD group exhibited better effect. All results are consistent with the anti-tumour effect.

Conclusion: The nRGD group can significantly improve the efficacy of the drug whether it is directly mixed with doxorubicin and its liposomes or modified on the surface of liposomes. It should be noticed that the addition of nRGD has resulted in very significant effect, thereby reducing the number of doses and achieving excellent therapeutic effects.

Figures 2, 3, 4:
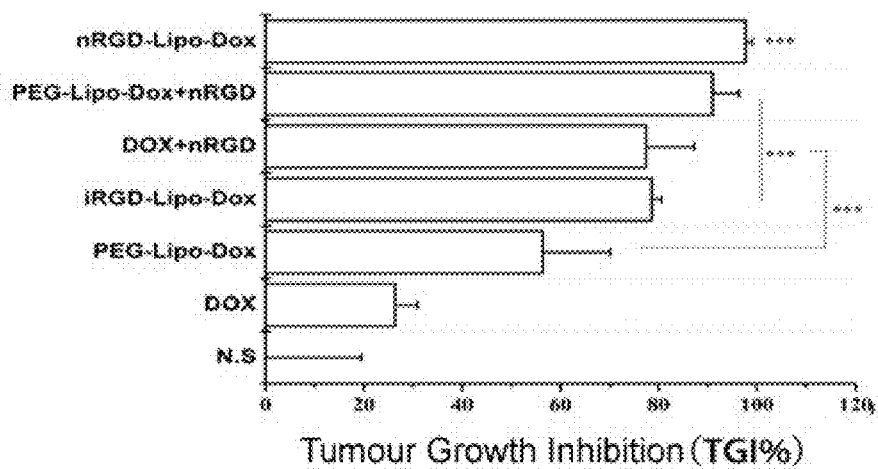

2. The nRGD group targeted tumour vessels and cells while targeting TAMs, as shown in FIG. 4 and Table 2.

The targeting ability of nRGD was studied through in vitro and in vivo experiments by the inventors. Cell uptake experiments (FIG. 4-1, FIG. 4-2, FIG. 4-3) demonstrated that nRGD-Lipo-Dox selectively targeted $CoCl_2$-stimulated 4T1 cells with activated legumain expression and M4 macrophage stimulated by IL-4. At the same time, in the HUVEC with low legumain expression and untreated 4T1 cells, the uptake of nRGD was significantly reduced compared to iRGD. As shown in Table 2, IC50 values in each group were consistent with cell uptake results. The IC50 of nRGD-Lipo-Dox group was lower in $CoCl_2$-stimulated 4T1 cells and IL-2 stimulated M2 macrophages, indicating that it was more lethal to legumain-expressing cells.

Figures 2, 3, 4, 5:
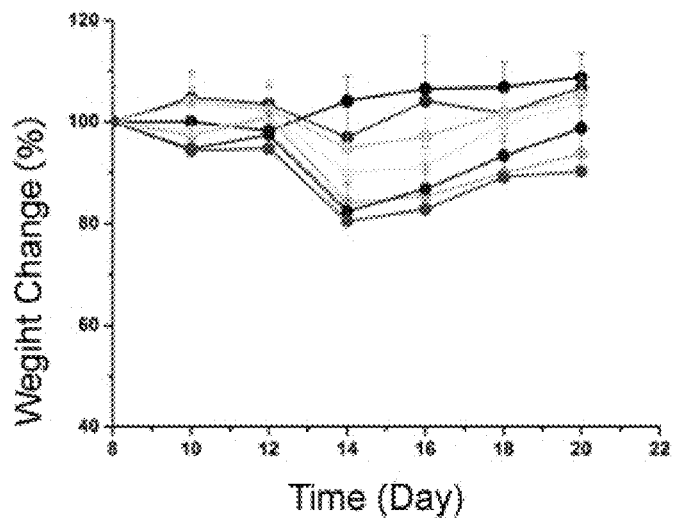

The inventors also evaluated the in vivo targeting ability of the nRGD group. As shown in FIG. 4-4, co-administration with nRGD or modification by nRGD both increased the accumulation of Dox in the tumour site, indicating that nRGD increased the drug's permeability at the tumour site. It can be seen from the sections that due to the killing of tumour cells by Dox and liposomes, cavities appeared in the infiltrated tumours and only connective tissues of the tumour stroma remained. The inventors evaluated the antiangiogenic effect and found that the tumour vessels gradually decreased in the nRGD group and the iRGD-Lipo-Dox group with the increase of time. Compared with saline group, Dox group and PEG-Lipo-Dox group, tumour-associated blood vessels in nRGD group and iRGD-Lipo-Dox group were significantly decreased. However, anti-angiogenesis and direct killing of tumour by drugs often lead to the accumulation of tumour-associated macrophage at the tumour sites. Previous studies have shown that the nRGD group and the iRGD-Lipo-Dox group exhibited rapid destruction of blood vessels and tumour cells at the tumour sites. As shown in FIG. 4-5, TAMs gradually increased over time in the iRGD-Lipo-Dox tumour sites as expected. The nRGD group, as described by the inventors, exhibited M2 macrophage killing effect without an increase of TAMs.

These results all confirmed that nRGD targets tumour vessels and tumour cells and has the effect of targeting TAMs.

Figures 2, 3, 4, 5, 6:
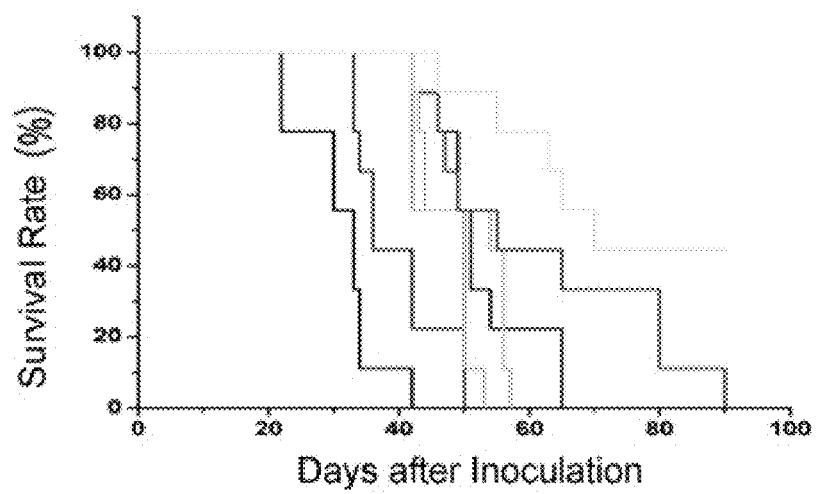
Figures 1, 3:
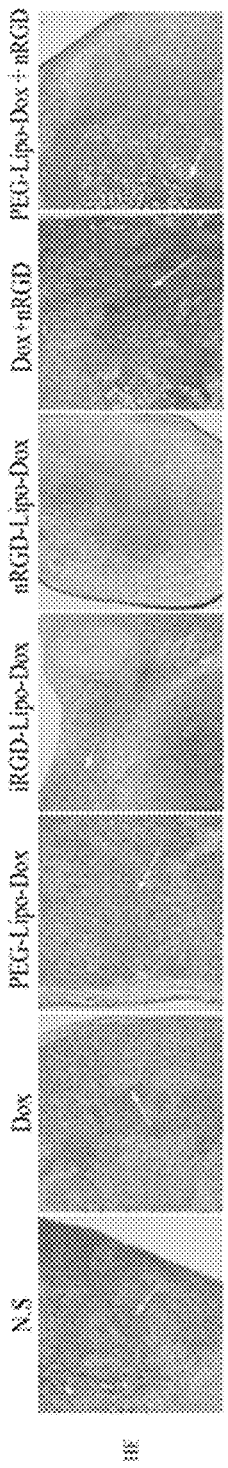
Figures 2, 3:
Figure 3:
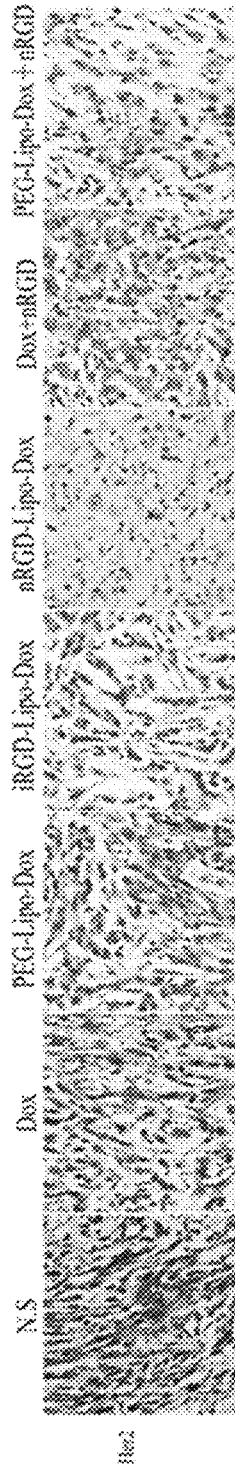
Figures 3, 4:
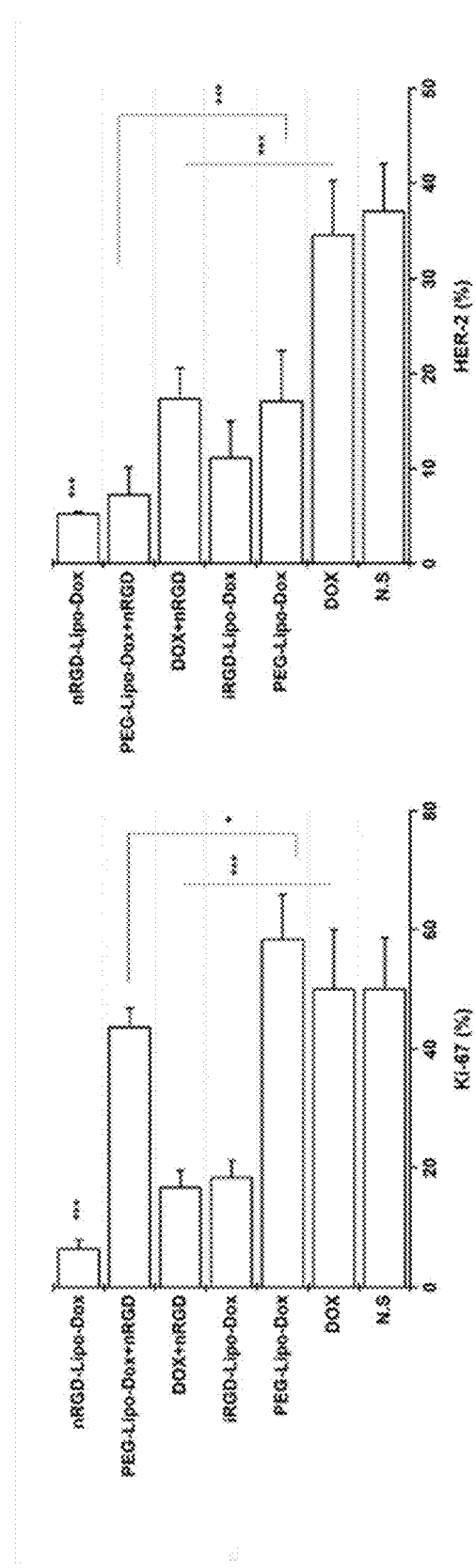
Figures 1, 4:
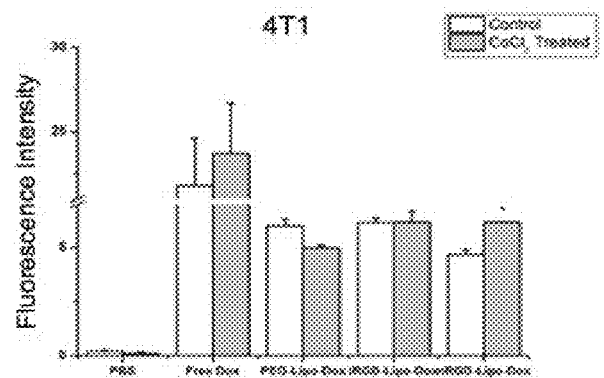
Figures 2, 4:
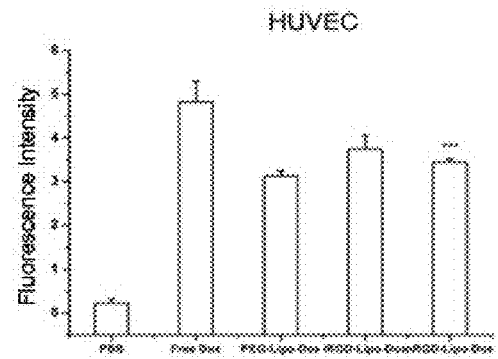
Figures 3, 4:
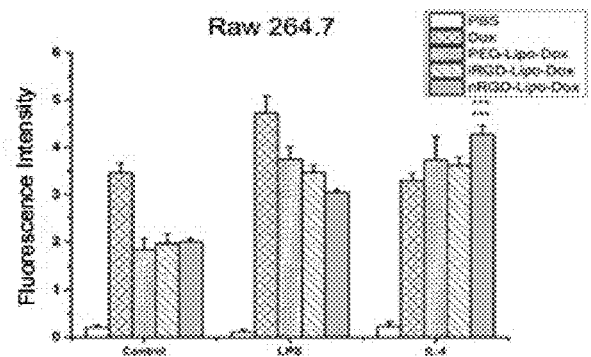
Figure 4:
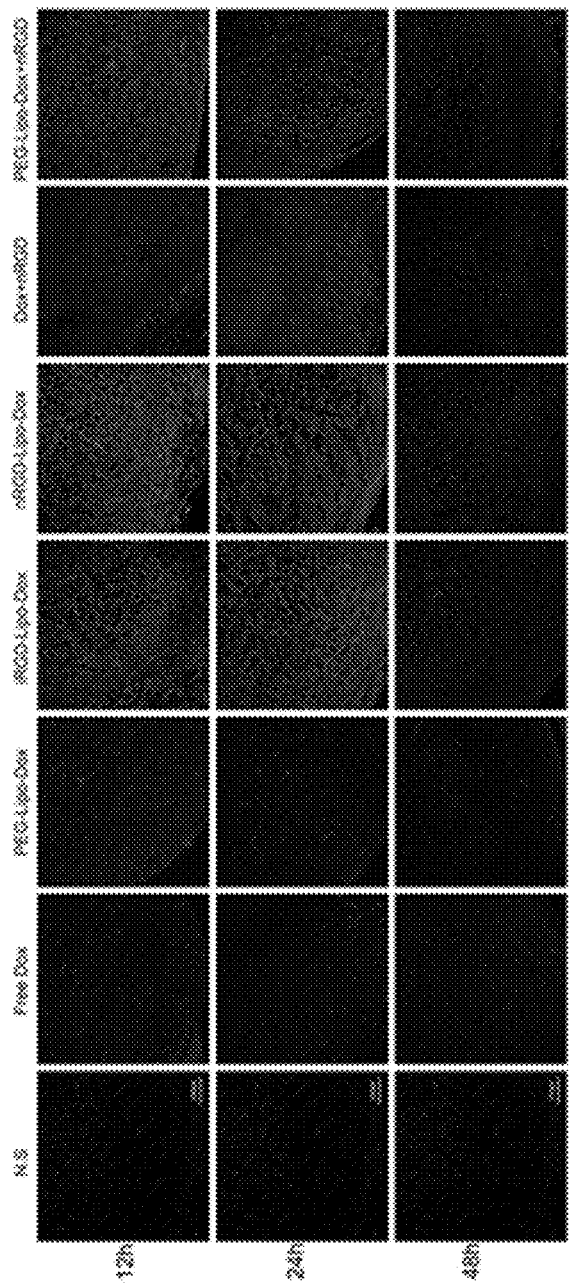
Figures 4, 5:
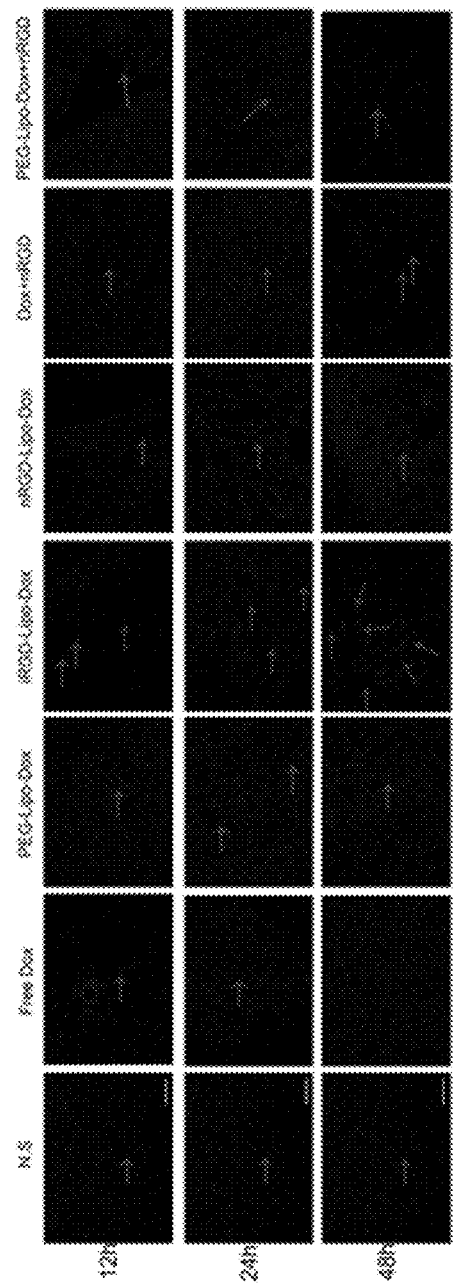
Figures 1, 5:
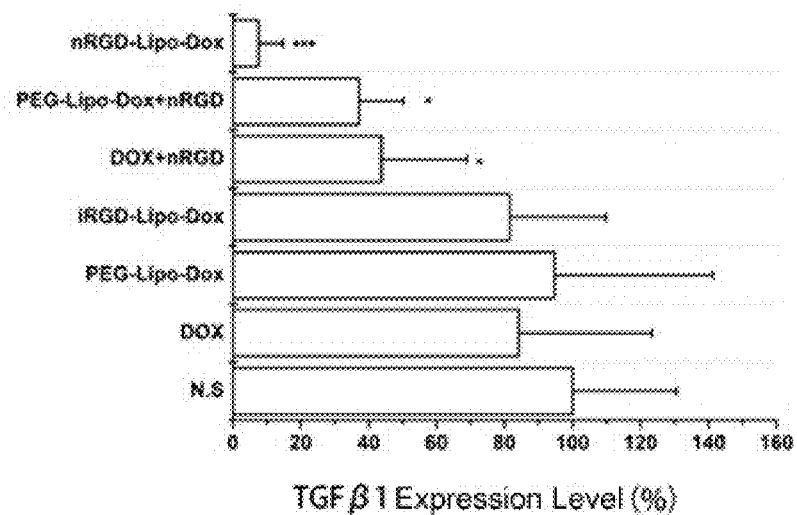
Figures 2, 5:
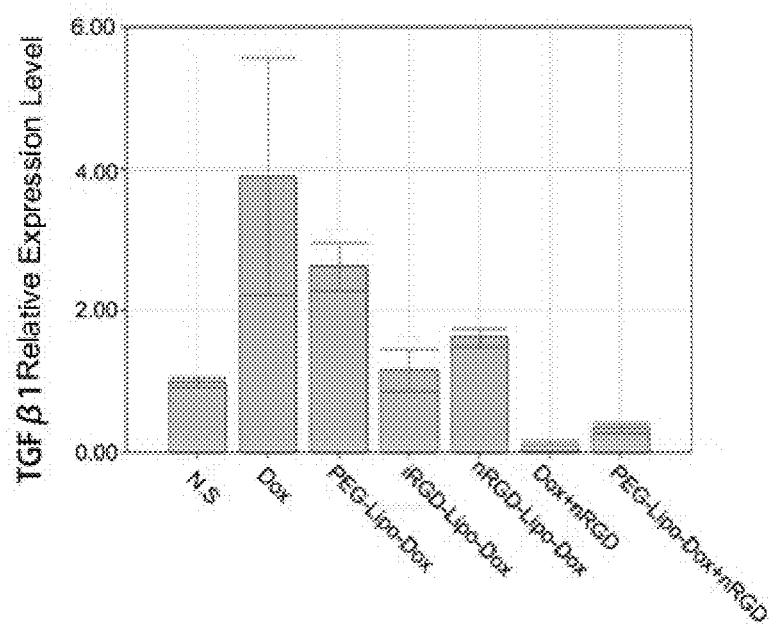
Figures 3, 5:
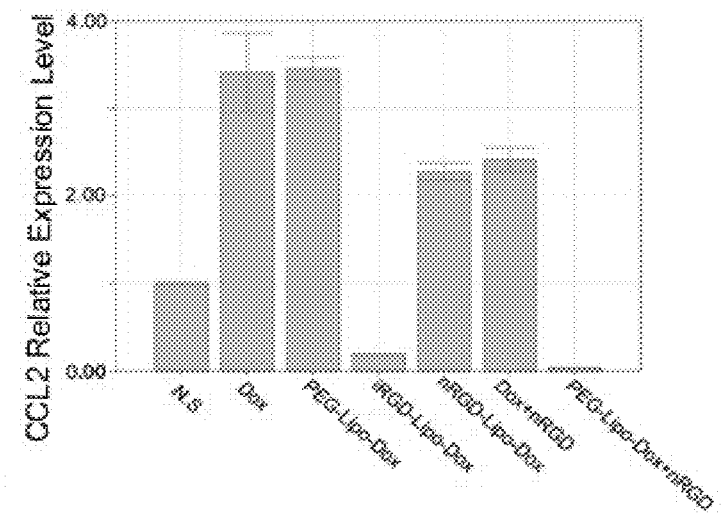
Figures 4, 5:
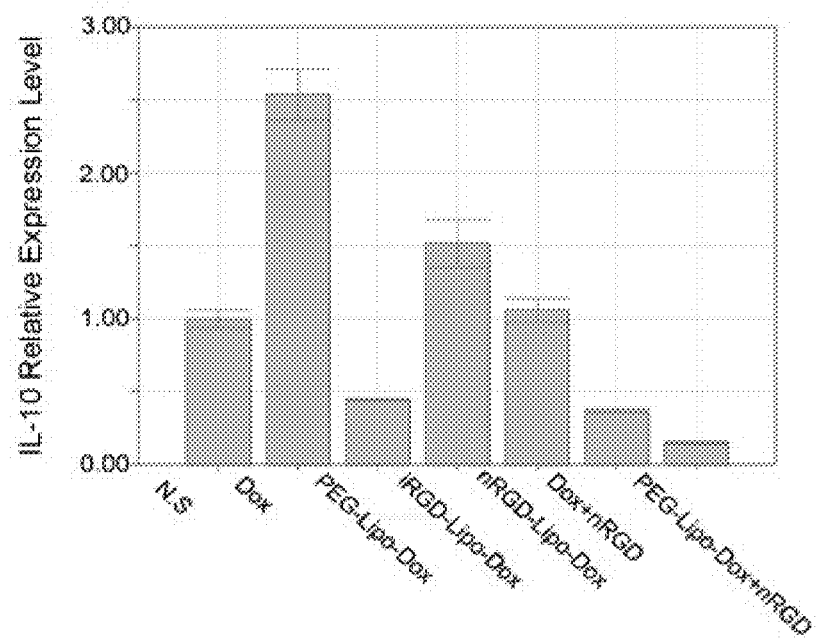
Figure 5:
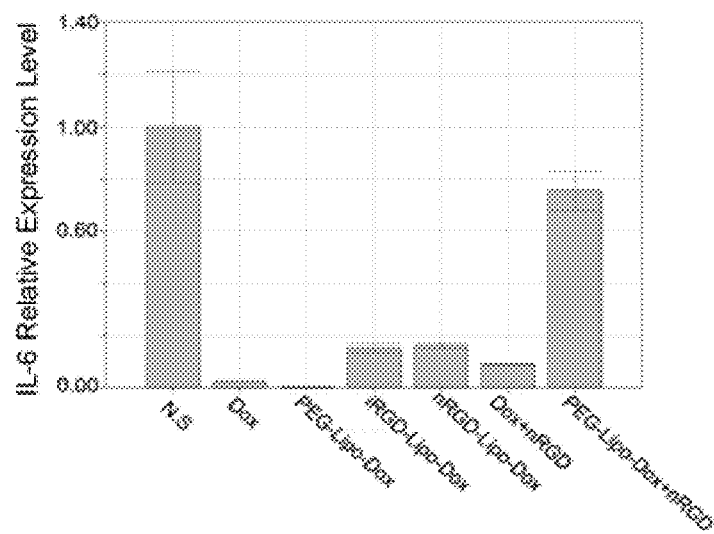
Figures 5, 6:
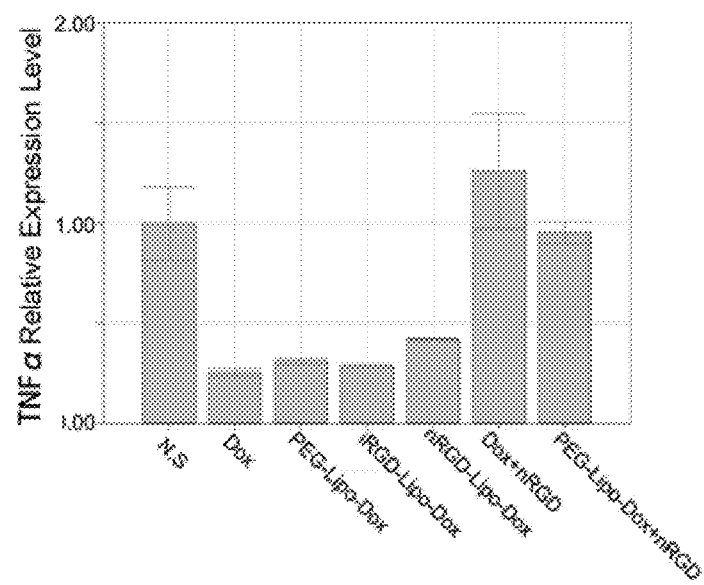
Figures 1, 6:
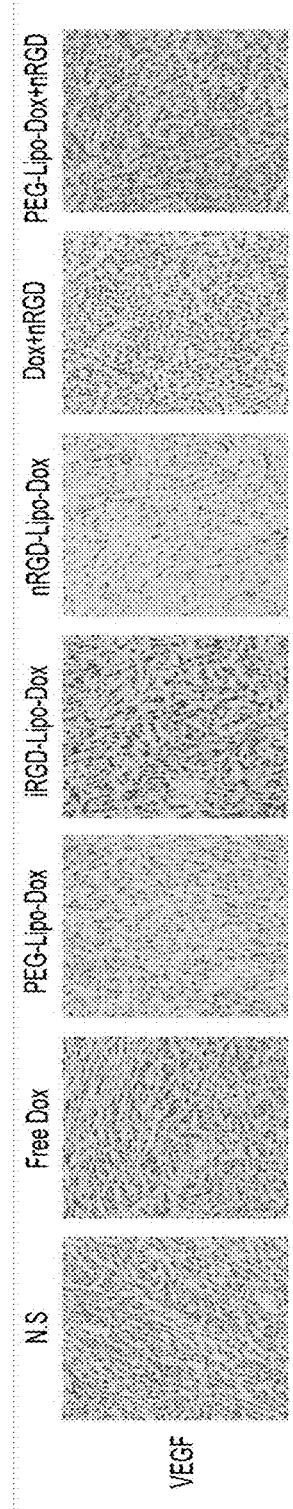
Figures 2, 6:
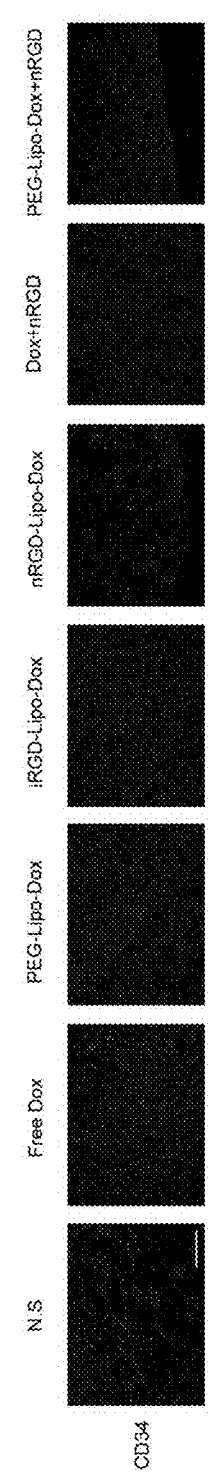
Figures 3, 6:
Figures 4, 6:
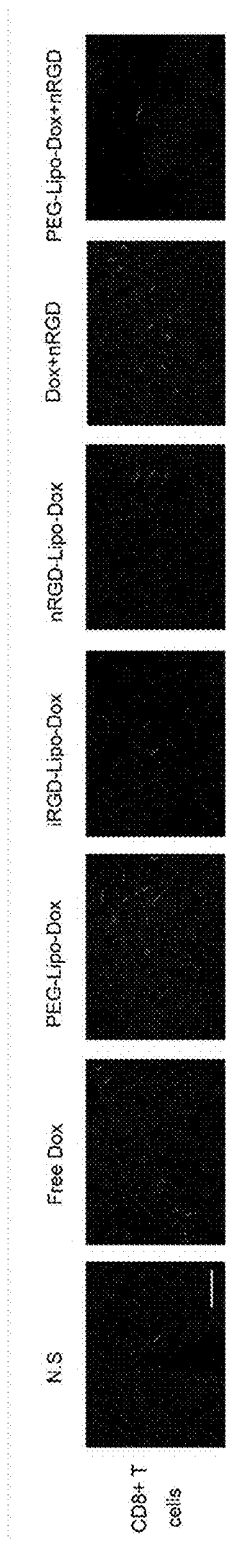
Figures 5, 6:
Figure 6:

3. The nRGD group targeted TAMs to regulate the tumour microenvironment, as shown in FIG. 5 and FIG. 6.

As described in the "Summary" part of the present disclosure, targeting of TAMs by nRGD is important for the regulation of the tumour microenvironment. The inventors have studied changes in the tumour microenvironment.

First, the inventors studied the level of cytokines at the tumour sites. TAMs are reported to be cells that express high levels of TGFβ1, CCl2, and IL-10. As shown in FIG. 5, the expression levels of all three cytokines in the nRGD group were reduced. In contrast, the expression levels of IL-6 and TNF-α in the nRGD group increased, which can help to suppress the effect of the effector T cells and thus suppress the immune response at the tumour sites. The results showed that the change of cytokines in the tumour sites of the nRGD group was helpful to improve its function on tumours treatment.

Since targeting of TAMs can help to normalize tumour angiogenesis and thereby improve the therapeutic efficacy, the inventors studied vascular endothelial growth factor (VEGF), CD34-labeled tumour vessels, and CD 105-labeled tumour neovascularization. As shown in FIGS. 6-1, 6-2 and 6-3, the nRGD group has relatively low VEGF expression with a decrease in blood vessels and neovascularization at the tumour sites. While in the iRGD-Lipo-Dox group, although the number of blood vessels decreased, the expression of VEGF and neovascularization increased. The above results indicated that tumour blood vessels remained normal after targeting of TAMs by nRGD, thereby inhibiting tumour angiogenesis and recurrence of tumour.

TAMs are also involved in immune escape and inhibition at the tumour sites. The inventors studied the number of immune cells at the tumour sites. As shown in FIG. 6-4, there is no clear pattern of the change of CD8+ T cells. As shown in FIGS. 6-5 and 6-6, the number of regulatory T cells and MDSCs in the Dox group, the PEG-Lipo-Dox group and the iRGD-Lipo-Dox group increased at the tumour sites, but there was no change in the nRGD group. These results indicated that the nRGD group targeted TAMs, thereby reducing the number of regulatory T cells and MDSCs, and suppressing the effects of these cells on tumour growth and tumour immune escape.

Figures 1, 7:
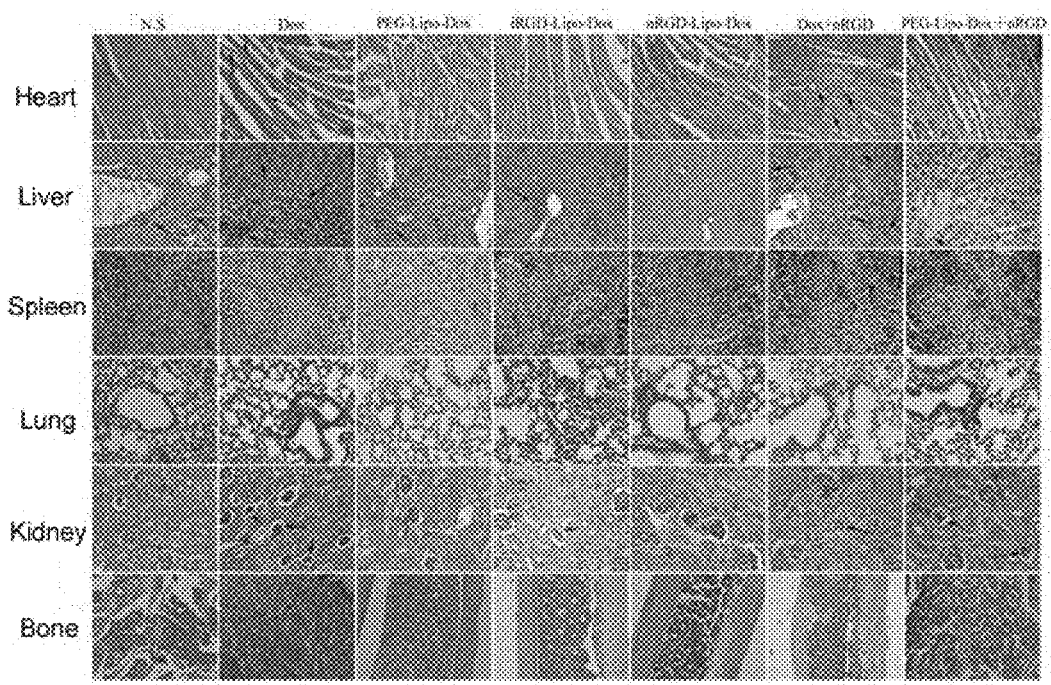
Figures 2, 7:
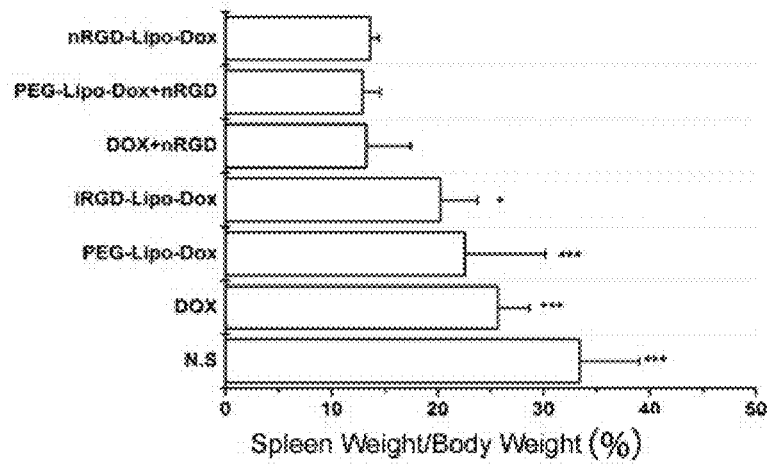
Figures 3, 7:
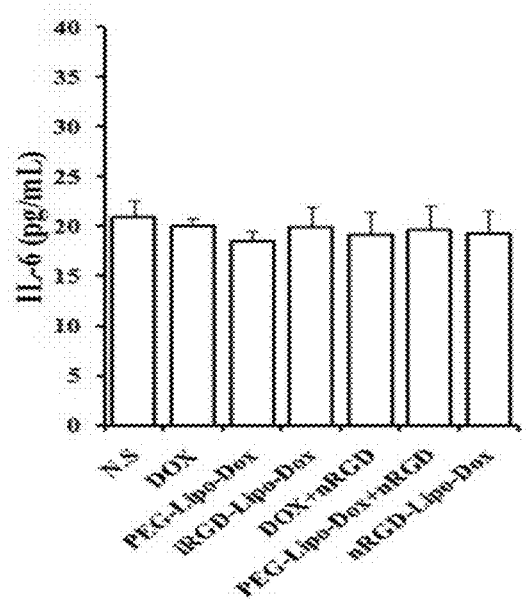
Figures 4, 7:
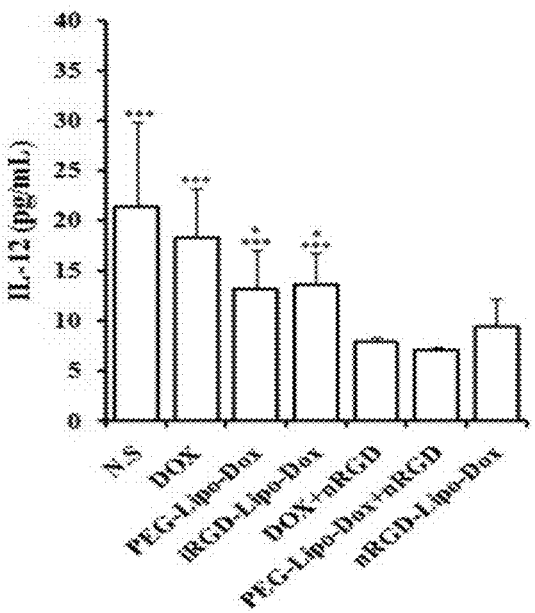

4. The nRGD group showed lower toxicity, as shown in FIG. 7.

For chemotherapeutic drugs, biosafety is an important aspect that needs attention and should not be ignored. The inventors evaluated the drug toxicity after administration. The inventors found that the addition of nRGD did not reduce the weight of mice. The study of organ sections found that the nRGD group has a reduced toxicity to the heart, kidney and liver, which may be related to its high targeting

TABLE 2

Median lethal dose (IC50) of Dox and liposomes against 4T1, HUVEC and Raw 264.7 cells at 24 h. (n = 3)

| | $IC_{50}$ Dox/(μg · mL$^{-1}$) | | | | | |
|---|---|---|---|---|---|---|
| | Raw264.7 | | | | 4T1 | |
| Entry | Control | LPS | IL-4 | HUVEC | control | $CoCl_2$ |
| Free DOX | 0.41 ± 0.08 | 0.81 ± 0.22 | 0.36 ± 0.07 | 18.12 ± 6.13 | 26.56 ± 1.96 | 16.54 ± 2.57 |
| PEG-Lipo-DOX | 57.75 ± 6.19 | 42.97 ± 4.82 | 49.62 ± 4.71 | 94.88 ± 6.69 | 49.48 ± 5.66 | 46.03 ± 1.78 |
| iRGD-Lipo-DOX | 16.72 ± 2.95 | 19.40 ± 3.71 | 29.04 ± 4.90 | 52.39 ± 5.74 | 33.30 ± 2.68 | 33.07 ± 2.32 |
| nRGD-Lipo-DOX | 32.65 ± 5.99 | 33.68 ± 5.61 | 23.50 ± 0.97 | 49.64 ± 6.39 | 69.75 ± 8.76 | 37.88 ± 5.48 | ability and distribution change in the body. The nRGD group has a reduced systemic toxicity and the data showed that the nRGD group has a lower spleen weight. Cytokine IL-6 and IL-12 assays also showed that serum levels of IL-6 and IL-12 were reduced in the nRGD group.

In summary, the nRGD group achieved excellent anti-tumour effects and showed lower toxicity by targeting tumour vessels, tumour cells and TAMs to regulate the tumour microenvironment.

Example 4

Figures 1, 8:
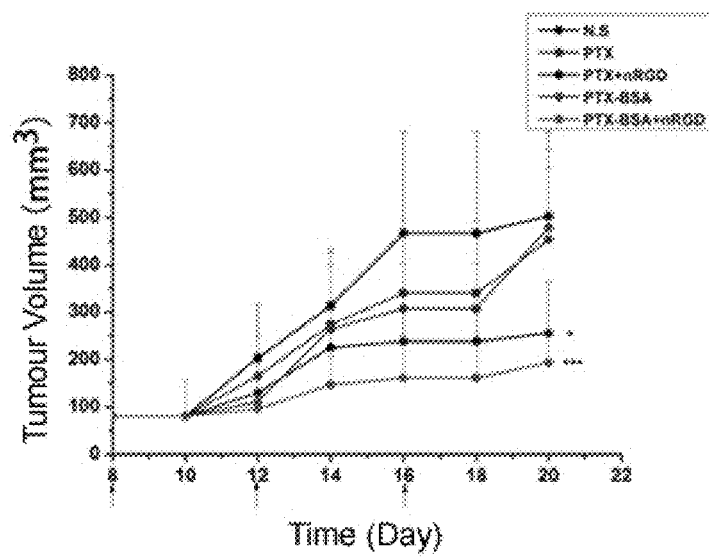
Figures 2, 8:
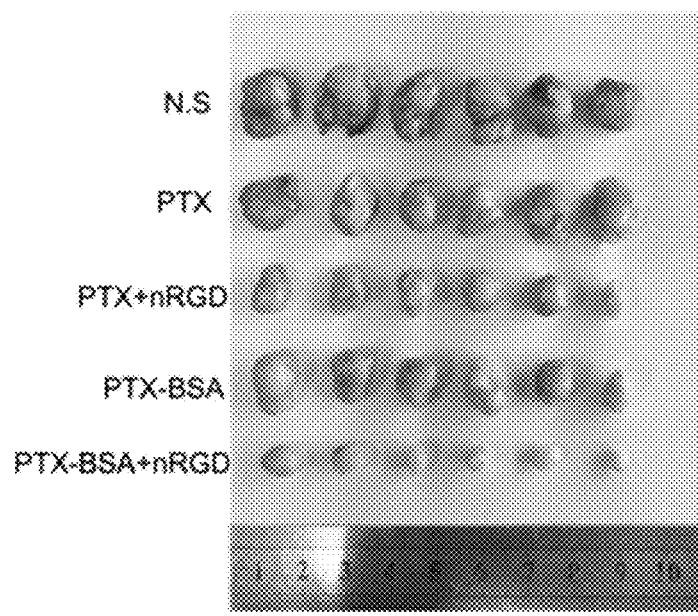
Figures 3, 8:
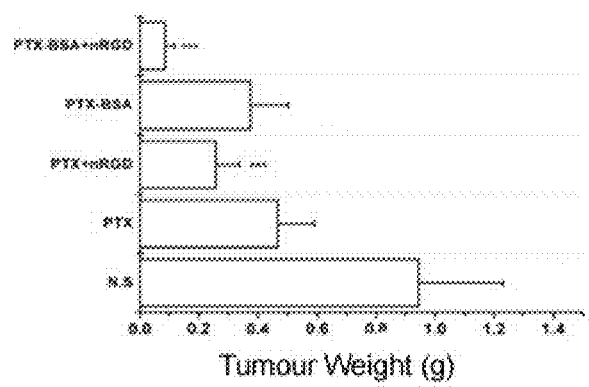
Figures 4, 8:
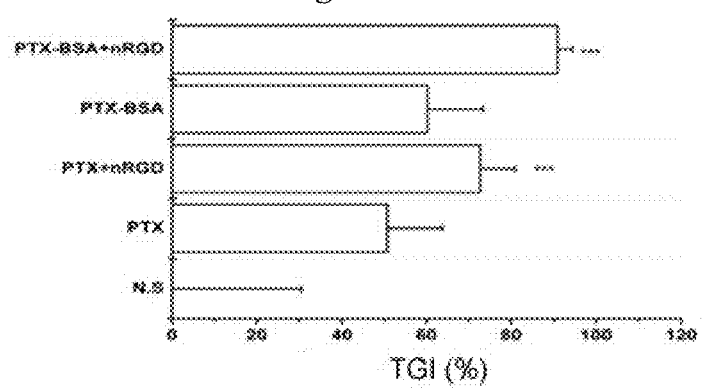
Figures 5, 8:
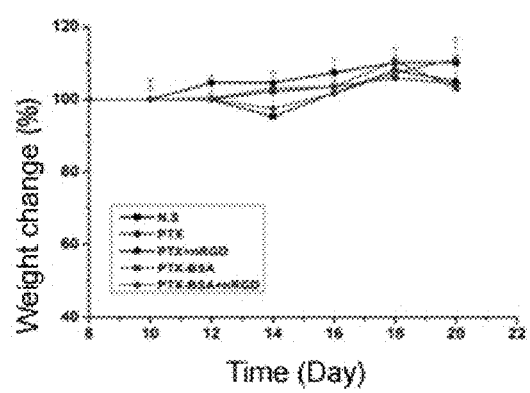

Evaluation of Pharmacodynamics of Paclitaxel (PTX) and its Albumin Nanoparticles Female Balb/c mice were inoculated with $5\times10^5$ 4 T1 cells and randomly divided into 5 groups: normal saline group (N. S), PTX group, paclitaxel albumin nanoparticle group (PTX-BSA), PTX and nRGD coadministration group (PTX+nRGD), and paclitaxel albumin nanoparticle and nRGD coadministration group (PTX-BSA+nRGD). The mice were injected with 10 mg/kg PTX equivalents of drugs or various formulations on day 8, day 12 and day 16. The single dose of the coadministration group included two shoots; one shoot was an equivalent drug or formulation of 10 mg/kg PTX, while the other shoot was 4.8 mg/kg nRGD. The volume and body weight of the mice were measured every two days. Some mice were sacrificed for mechanism and toxicity study on day 20. The average tumour growth inhibition (TGI) was calculated after tumour weighing: TGI=(1−(mean tumour weight of treatment group/(average tumour weight of control group))×100%.
Results:

As shown in FIG. 8, nRGD increased the anti-tumour efficacy of PTX and PTX-BSA, while did not reduce the body weight of the mice or increase the toxicity.

Example 5

Evaluation of Pharmacological Effects of Lycobetaine (IBT) and its Nanostructured Lipid Carriers (NLC)

Figures 1, 9:
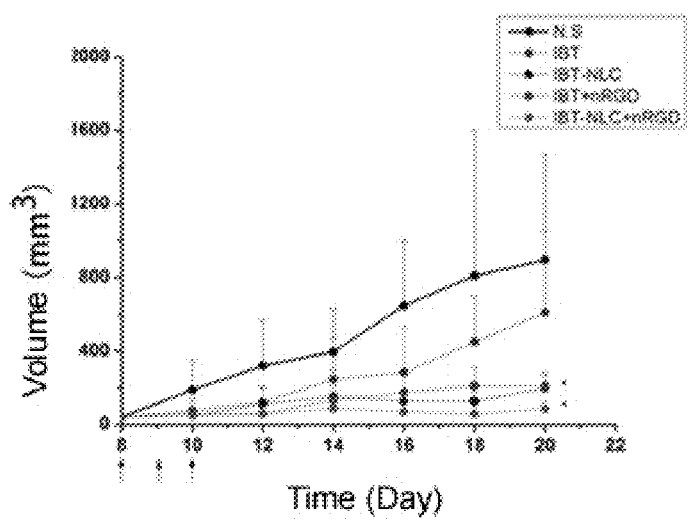
Figures 2, 9:
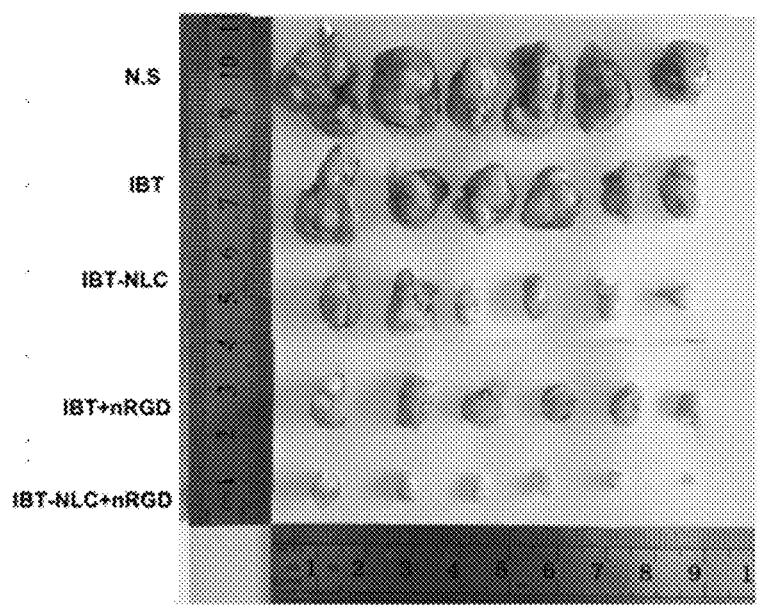
Figures 3, 9:
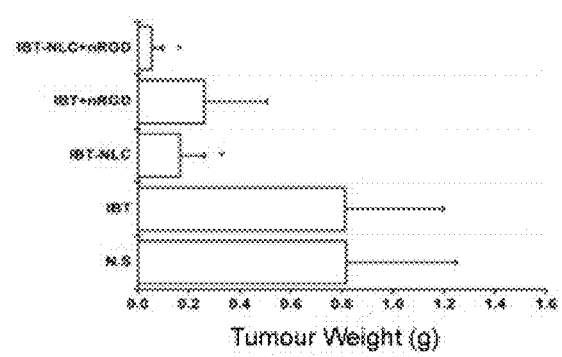
Figures 4, 9:
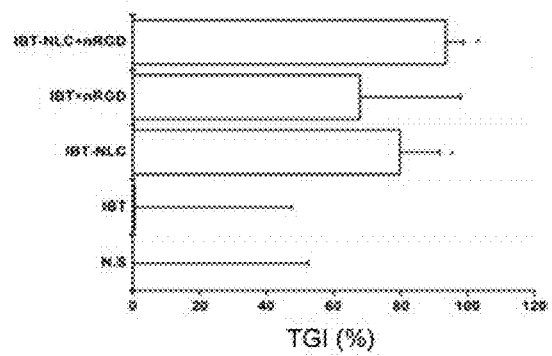
Figures 5, 9:
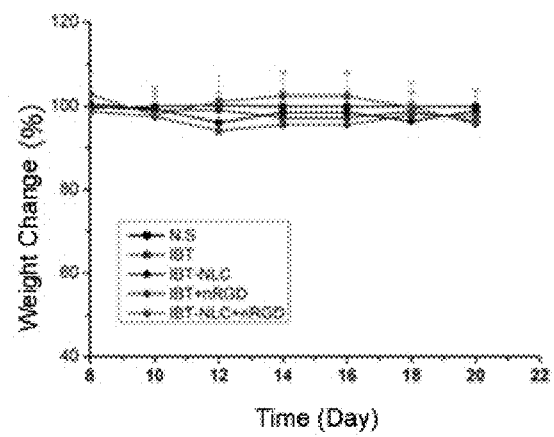

Female Balb/c mice were inoculated with $5\times10^5$ 4 T1 cells and randomly divided into 5 groups. Normal saline group (N. S), IBT group, lycobetaine nanostructured lipid carriers group (IBT-NLC), lycobetaine and nRGD coadministration group (IBT+nRGD), and lycobetaine nanostructured lipid carriers and nRGD coadministration group (IBT-NLC+nRGD). The mice were injected with 12 mg/kg IBT equivalents of drugs or various formulations on day 8, day 9 and day 10. The single dose of the coadministration group included two shoots; one shoot was an equivalent drug or formulation of 12 mg/kg IBT, while the other shoot was 4.8 mg/kg nRGD. The volume and body weight of the mice were measured every two days. Some mice were sacrificed for mechanism and toxicity study on day 20. The average tumour growth inhibition (TGI) was calculated after tumour weighing: TGI=(1−(mean tumour weight of treatment group/(average tumour weight of control group))×100%.
Results:

As shown in FIG. 9, nRGD increased the anti-tumour efficacy of PTX and PTX-BSA, while did not reduce the body weight of the mice or increase the toxicity.

Example 6

Evaluation of Pharmacological Effects of Docetaxel (TXT) and its Micells

Figures 1, 10:
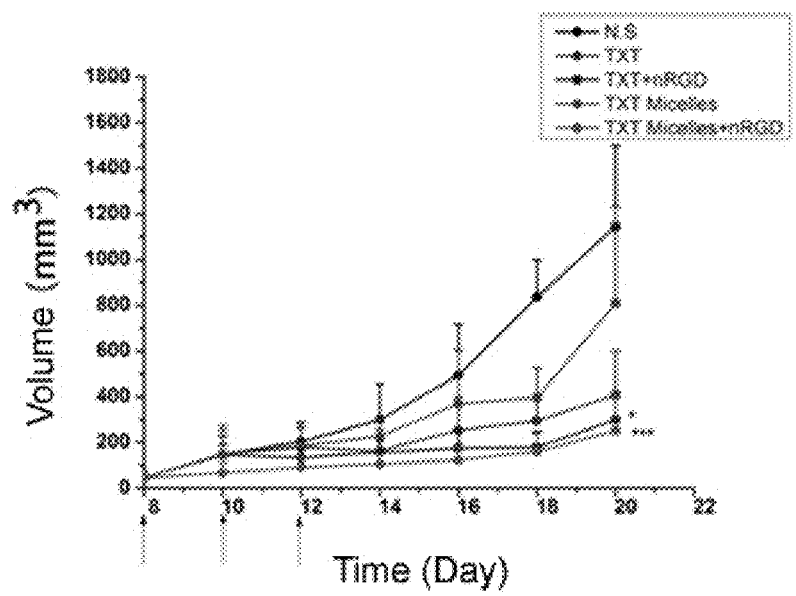
Figures 2, 10:
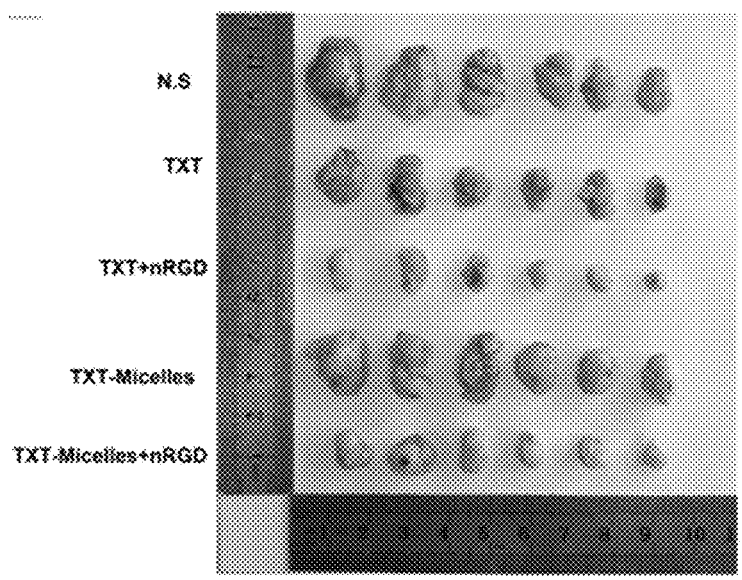
Figures 3, 10:
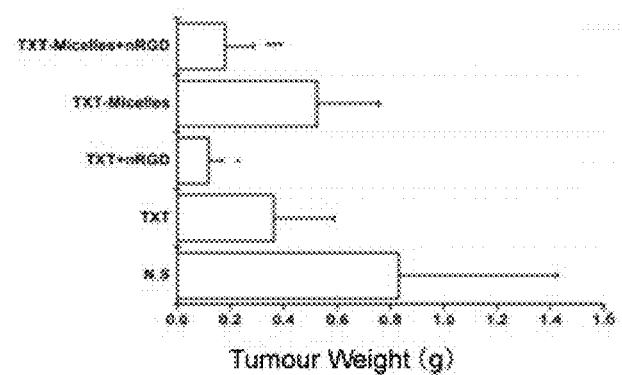
Figures 4, 10:
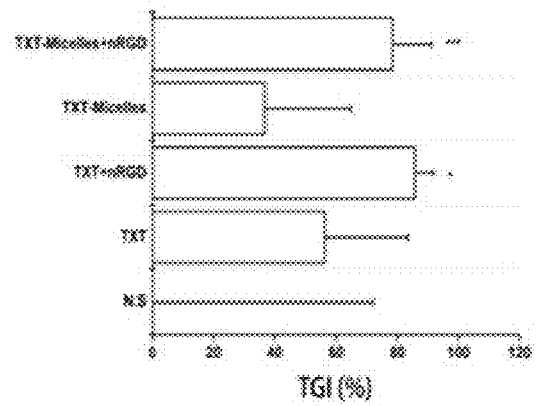
Figures 5, 10:
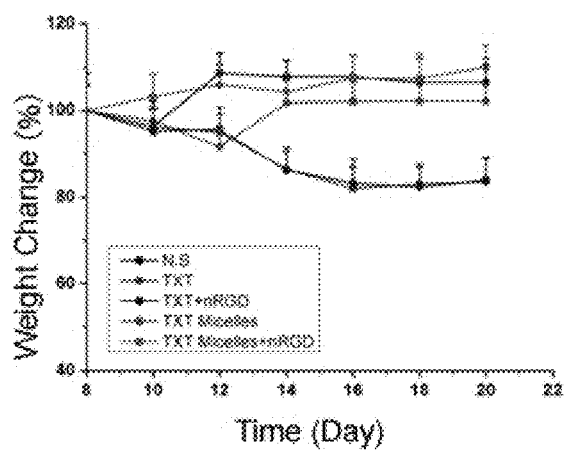

Female Balb/c mice were inoculated with $5\times10^5$ 4T1 cells and randomly divided into 5 groups: normal saline group (N. S), TXT group, docetaxel micells group (TXT-micells), docetaxel and nRGD coadministration group (TXT+nRGD), and docetaxel micells and nRGD coadministration group (TXT-micells+nRGD). The mice were injected with 15 mg/kg TXT equivalents of drugs or various formulations on day 8, day 10 and day 12. The single dose of the coadministration group included two shoots; one shoot was an equivalent drug or formulation of 15 mg/kg TXT, while the other shoot was 4.8 mg/kg nRGD. The volume and body weight of the mice were measured every 2 days. Some mice were sacrificed for mechanism and toxicity study on day 20. The average tumour growth inhibition (TGI) rate was calculated after tumour weighing: TGI=(1−(mean tumour weight of treatment group/(average tumour weight of control group))×100%.
Results:

As shown in FIG. 10, nRGD increased the anti-tumour efficacy of TXT and TXT-micells, while did not reduce the body weight of the mice or increase the toxicity.

Example 7

In the glioma model, the nRGD group showed better anti-tumour effects than the iRGD group.

Figure 11:
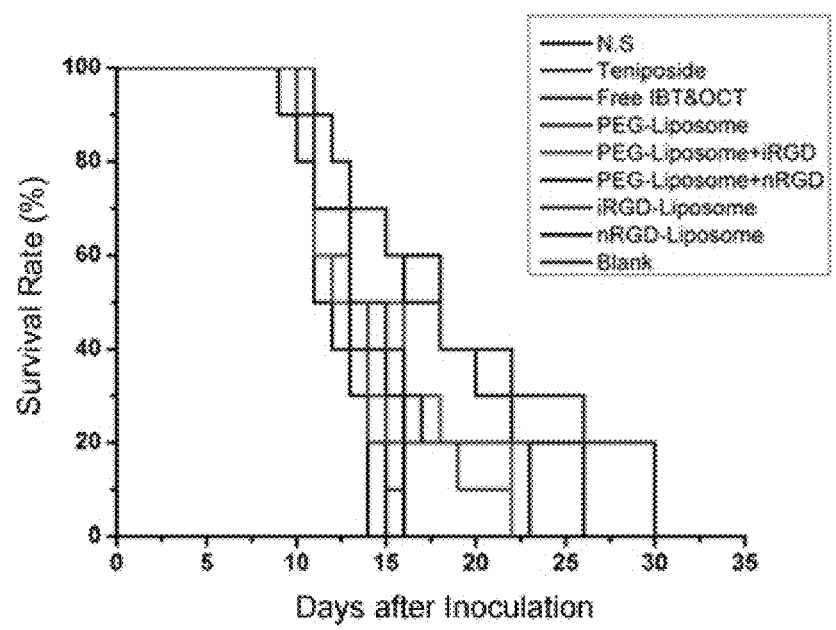
FIG. 11 shows that in the glioma model, the nRGD group has a better anti-tumour effect than the iRGD group.

Mice having glioma were randomly divided into 9 groups, 20 mice each: normal saline group (N.S), teniposide group, free lycobetaine and octreotide group (free IBT & OCT), lycobetaine and octreotide PEGylated liposomes group (PEG-Liposome), liposomes and iRGD coadministration group (PEG-Liposome+iRGD), liposomes and nRGD coadministration group (PEG-Liposome+nRGD), iRGD modified lycobetaine and octreotide PEGylated liposomes (iRGD-Liposome), nRGD modified lycobetaine and octreotide PEGylated liposomes (nRGD-Liposome), liposomes and nRGD coadministration group (blank). The mice were injected with 10 mg/kg IBT and 200 m/kg OCT equivalents of drugs or various formulations on day 5, day 7, day 9, day 11 and day 12. As positive control group, mice were injected with 10 mg/kg teniposide on day 5, day 7, day 9, day 11 and day 12. The single dose of the coadministration group included two shoots; one shoot was an equivalent drug or formulation of 10 mg/kg IBT and 200 m/kg OCT, while the other shoot was 5 mg/kg iRGD or nRGD. The survival of the mice was recorded daily and the survival curve was plotted.
Results:

As shown in FIG. 11, in the mouse glioma model, the nRGD group had a longer life period than the iRGD group, whether nRGD was administered as a mixture or modified on the liposome surface. Thus, the nRGD group has a better anti-tumour effect than the iRGD group no matter nRGD was administered as a mixture or modified on the liposome surface.

Example 8

The inventors screened the administration manner of nRGD by using doxorubicin as a model drug.

Female Balb/c mice were inoculated with $5\times10^5$ 4 T1 cells and randomly divided into 3 groups. nRGD was administered in combination with doxorubicin, nRGD was administered prior to doxorubicin or after doxorubicin.
Results:

There were no significant differences in the anti-tumour effects of different manners of administration.

Example 9

The inventors screened the working concentration of nRGD by using doxorubicin as a model drug.

Female Balb/c mice were inoculated with $5 \times 10^5$ 4T1 cells and randomly divided into 5 groups. The dose of doxorubicin was 5 mg/kg, while the nRGD concentration was 1, 2, 4, 8, 10 mg/kg, respectively.

Results:

The concentration of nRGD was positively correlated with Dox antitumour efficacy.

Example 10

Polypeptides were synthesized by solid phase synthesis (Synthesized by GL Biochem. (Shanghai) LTD.). The peptide sequences RGD and c(RGDfK) (SEQ ID NO: 1), which target the integrin receptor of tumour neovascular endothelial cells, were linked to AAN by peptide bond, respectively. The resulting sequences were CRGDNAA (SEQ ID NO: 5) and c(RGDfK)AAN (SEQ ID NO: 6). The evaluation of these two peptides is as follows:

Female Balb/c mice were inoculated with $5 \times 10^5$ 4T1 cells and randomly divided into 3 groups. The dose of doxorubicin was 5 mg/kg for all groups. Two groups were administrated with above-mentioned peptides, respectively.

Results:

Both CRGDNAA (SEQ ID NO: 5) and c(RGDfK)AAN (SEQ ID NO: 6) can improve the efficacy of doxorubicin.

Example 11

Polypeptides were synthesized by solid phase synthesis (Synthesized by GL Biochem. (Shanghai) LTD.). The peptide sequences RGD and c(RGDfK), which target the integrin receptor of tumour neovascular endothelial cells, were linked to AAN by —NHCH$_2$CH$_2$CH$_2$CO—, respectively. The resulting sequences were CRGD-4Abu-NAA (SEQ ID NO: 7) and c(RGDfK)-4Abu-AAN (SEQ ID NO: 8). The evaluation of these two peptides is as follows:

Female Balb/c mice were inoculated with $5 \times 10^5$ 4T1 cells and randomly divided into 3 groups. The dose of doxorubicin was 5 mg/kg for all groups. Two groups were administrated with above-mentioned peptides, respectively.

Results:

Both CRGD-4Abu-NAA (SEQ ID NO: 7) and c(RGDfK)-4Abu-AAN (SEQ ID NO: 8) can improve the efficacy of doxorubicin.

In summary, the nRGD of the present invention significantly increases the effect of antitumour drugs, with lower toxicity and wide applicability, which has not been reported in prior literature and data. The inventors have reasonably speculated that the present invention can be used in a variety of anti-tumour compositions and also in combination with antitumour auxiliary molecules to improve their therapeutic effects on malignant or benign tumours.

The invention claimed is:

1. A polypeptide nRGD, wherein an alanine-alanine-asparagine (AAN)-containing sequence is linked to an RGD-containing peptide, wherein the AAN-containing sequence is linked to the RGD-containing peptide by CH2NH—, —CH2S—, —CH2-CH2-, —CH=CH— or —CH(OH)CH2-.

2. The polypeptide nRGD according to claim 1, wherein the RGD-containing peptide in the nRGD polypeptide is selected from the group consisting of RGD peptide, cyclic c(RGDfK) (SEQ ID NO:1) and iRGD (SEQ ID NO:2).

3. The polypeptide nRGD according to claim 1, wherein the alanine-alanine-asparagine (AAN)-containing sequence includes polypeptide substrate R-AAN sequence which is susceptible to legumain, wherein the R group is hydrogen atom (H), acetyl group (Ac), alanine (A), phenylalanine (F), glycine (G), or a conjugate thereof.

4. A polypeptide nRGD, wherein an alanine-alanine-asparagine (AAN)-containing sequence is linked to an RGD-containing peptide, wherein
the polypeptide nRGD has a sequence of CCRGDK(NAA)GPDC (SEQ ID NO: 3), wherein the second cysteine and the tenth cysteine are linked into a ring; or
the polypeptide nRGD has a sequence of CRGDK(NAA)GPDC (SEQ ID NO: 4), wherein the two cysteines are linked into a ring.

5. A pharmaceutical composition, comprising the polypeptide nRGD according to claim 1 and an active pharmaceutical ingredient, or comprising the polypeptide nRGD according to claim 1 and a drug delivery carrier.

6. The pharmaceutical composition according to claim 5, wherein the polypeptide nRGD is either covalently linked to or non-covalently associated with the active pharmaceutical ingredient, or the polypeptide nRGD is either covalently linked to or non-covalently associated with the drug delivery carrier.

7. The pharmaceutical composition according to claim 5, wherein the polypeptide nRGD can be used in combination with one or more auxiliary molecule.

8. A method for treating tumours, comprising administrating the polypeptide nRGD according to claim 1 or a pharmaceutical composition comprising the polypeptide nRGD according to claim 1 and an active pharmaceutical ingredient, or comprising the polypeptide nRGD according to claim 1 and a drug delivery carrier, to a subject in need thereof.

9. The method according to claim 8, wherein the tumours include benign or malignant tumours of epithelial tissue; benign or malignant tumours of mesenchymal tissue; benign or malignant tumours of lymphoid and hematopoietic tissue; benign or malignant tumours of nervous tissue; gonad or embryo-related benign or malignant tumours; pigmented nevus, hydatidiform mole, melanoma, chorionic epithelioma, seminoma, dysgerminoma and embryonal carcinoma.

10. The pharmaceutical composition according to claim 7, wherein the auxiliary molecule includes separate homing molecule, targeting molecule, affinity ligand, cell penetrating peptide, in vivo escape molecule, subcellular targeting molecule, nuclear targeting molecule, or a conjugate and mixture thereof.

* * * * *

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<221> NAME/KEY: MISC_FEATURE
<223> OTHER INFORMATION: Cyclic

<400> SEQUENCE: 1

Arg Gly Asp Phe Lys
1               5

<210> SEQ ID NO 2
<211> LENGTH: 9
<212> TYPE: PRT
<213> ORGANISM: Artificial Sequence
<220> FEATURE:
<221> NAME/KEY: MISC_FEATURE
<223> OTHER INFORMATION: cyclic

<400> SEQUENCE: 2

Cys Arg Gly Asp Lys Gly Pro Asp Cys
1               5

<210> SEQ ID NO 3
<211> LENGTH: 10
<212> TYPE: PRT
<213> ORGANISM: Artificial Sequence
<220> FEATURE:
<221> NAME/KEY: MISC_FEATURE
<223> OTHER INFORMATION: The Gly at posision 7 is linked with "Ala Ala
      Asn" peptide
<220> FEATURE:
<221> NAME/KEY: DISULFID
<222> LOCATION: (2)..(10)
```

-continued

<400> SEQUENCE: 3

Cys Cys Arg Gly Asp Lys Gly Pro Asp Cys
1               5                   10

<210> SEQ ID NO 4
<211> LENGTH: 9
<212> TYPE: PRT
<213> ORGANISM: Artificial Sequence
<220> FEATURE:
<221> NAME/KEY: MISC_FEATURE
<223> OTHER INFORMATION: The Gly at position 6 is linked with "Ala Ala
      Asn" peptide
<220> FEATURE:
<221> NAME/KEY: DISULFID
<222> LOCATION: (1)..(9)

<400> SEQUENCE: 4

Cys Arg Gly Asp Lys Gly Pro Asp Cys
1               5

<210> SEQ ID NO 5
<211> LENGTH: 7
<212> TYPE: PRT
<213> ORGANISM: Artificial Sequence

<400> SEQUENCE: 5

Cys Arg Gly Asp Asn Ala Ala
1               5

<210> SEQ ID NO 6
<211> LENGTH: 8
<212> TYPE: PRT
<213> ORGANISM: Artificial Sequence
<220> FEATURE:
<221> NAME/KEY: MISC_FEATURE
<223> OTHER INFORMATION: RGDFK is cyclic

<400> SEQUENCE: 6

Arg Gly Asp Phe Lys Ala Ala Asn
1               5

<210> SEQ ID NO 7
<211> LENGTH: 7
<212> TYPE: PRT
<213> ORGANISM: artificial Sequence
<220> FEATURE:
<221> NAME/KEY: MISC_FEATURE
<223> OTHER INFORMATION: CRGD is linked to NAA by -NHCH2CH2CH2CO-

<400> SEQUENCE: 7

Cys Arg Gly Asp Asn Ala Ala
1               5

<210> SEQ ID NO 8
<211> LENGTH: 8
<212> TYPE: PRT
<213> ORGANISM: artificial Sequence
<220> FEATURE:
<221> NAME/KEY: MISC_FEATURE
<223> OTHER INFORMATION: cyclic RGDfK is linked to AAN by
      -NHCH2CH2CH2CO-

<400> SEQUENCE: 8

Arg Gly Asp Phe Lys Ala Ala Asn
1               5